US008106357B2

(12) United States Patent
Nakahira et al.

(10) Patent No.: US 8,106,357 B2
(45) Date of Patent: Jan. 31, 2012

(54) SCANNING ELECTRON MICROSCOPE AND METHOD FOR PROCESSING AN IMAGE OBTAINED BY THE SCANNING ELECTRON MICROSCOPE

(75) Inventors: Kenji Nakahira, Fujisawa (JP); Toshifumi Honda, Yokohama (JP); Atsushi Miyamoto, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 101 days.

(21) Appl. No.: 12/016,290

(22) Filed: Jan. 18, 2008

(65) Prior Publication Data
US 2008/0251719 A1 Oct. 16, 2008

(30) Foreign Application Priority Data

Jan. 19, 2007 (JP) ................................. 2007-009699

(51) Int. Cl.
*G01N 23/00* (2006.01)
(52) U.S. Cl. ........ 250/311; 250/306; 250/307; 250/310; 250/399; 250/492.3; 382/100; 382/141; 382/145; 382/149
(58) Field of Classification Search .................. 250/306, 250/307, 310, 311, 396 R, 397, 399, 492.1, 250/492.2, 492.3; 382/100, 141, 145, 149
See application file for complete search history.

(56) References Cited

U.S. PATENT DOCUMENTS

| | | | | |
|---|---|---|---|---|
| 5,576,548 A | * | 11/1996 | Clarke et al. ............... | 250/369 |
| 6,140,644 A | | 10/2000 | Kawanami et al. | |
| 6,239,909 B1 | * | 5/2001 | Hayashi et al. ............ | 359/569 |
| 6,452,635 B1 | * | 9/2002 | Tanaka ...................... | 348/342 |
| 6,578,188 B1 | * | 6/2003 | Pang et al. ................. | 716/19 |
| 7,598,492 B1 | * | 10/2009 | Krzeczowski et al. ...... | 250/310 |
| 7,860,675 B2 | * | 12/2010 | Miyano ....................... | 702/70 |
| 2004/0243320 A1 | * | 12/2004 | Chang et al. ............... | 702/30 |
| 2005/0117148 A1 | * | 6/2005 | Dirksen et al. ............. | 356/124 |
| 2005/0145792 A1 | * | 7/2005 | Nakazawa et al. ......... | 250/311 |

(Continued)

FOREIGN PATENT DOCUMENTS

JP 03-044613 2/1991
(Continued)

OTHER PUBLICATIONS

A. K. Katsaggelos: "Iterative image restoration algorithms", Optical Engineering, 28, 7, pp. 735-748 (Jul. 1989).
(Continued)

*Primary Examiner* — Robert Kim
*Assistant Examiner* — Michael Logie
(74) *Attorney, Agent, or Firm* — Antonelli, Terry, Stout & Kraus, LLP.

(57) ABSTRACT

In the case where a specimen is imaged by a scanning electron microscope, it is intended to acquire an image of a high quality having a noise component reduced, thereby to improve the precision of an image processing. The intensity distribution of a beam is calculated on the basis of an imaging condition or specimen information, and an image restoration is performed by using a resolving power deterioration factor other than the beam intensity distribution as a target of a deterioration mode, so that a high resolving power image can be acquired under various conditions. In the scanning electron microscope for semiconductor inspections and semiconductor measurements, the restored image is used for pattern size measurement, defect detections, defect classifications and so on, so that the measurements can be improved in precision and so that the defect detections and classifications can be made high precise.

11 Claims, 16 Drawing Sheets

U.S. PATENT DOCUMENTS

| | | | |
|---|---|---|---|
| 2005/0220332 A1* | 10/2005 | Akutagawa et al. | 382/144 |
| 2007/0146873 A1* | 6/2007 | Ortyn et al. | 359/386 |
| 2008/0226152 A1* | 9/2008 | Dirksen et al. | 382/141 |

FOREIGN PATENT DOCUMENTS

| | | |
|---|---|---|
| JP | 11-040096 A | 2/1999 |
| JP | 2001-015055 | 1/2001 |
| JP | 2002-075262 A | 3/2002 |
| JP | 2004-038362 A | 2/2004 |

OTHER PUBLICATIONS

M. R. Banham and A. K. Katsaggelos: "Digital Image Restoration", IEEE Signal Processing Magazine, pp. 24-41 (Mar. 1997).

Y. I. Gold and A. Goldenshtein: "SEM Image Sharpening by Reserving the Effect of Non-ideal Beam Spot", Proc. SPIE, 3332, pp. 620-624 (1998).

J. Orloff: Handbook of Charged Particle Optics, CRC Press (1997).

* cited by examiner

FIG. 10A     FIG. 10B
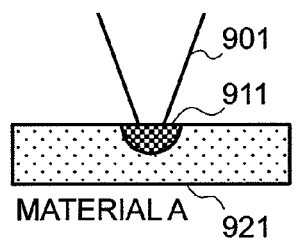 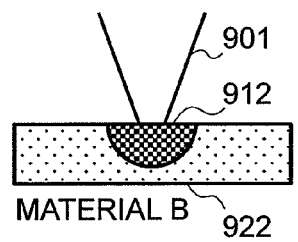
FIG. 10C
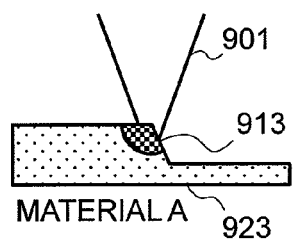
FIG. 11A     FIG. 11B     FIG. 11C
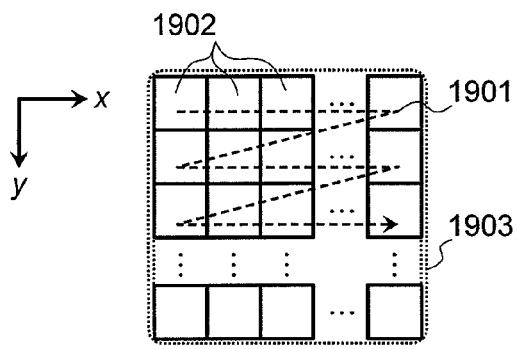 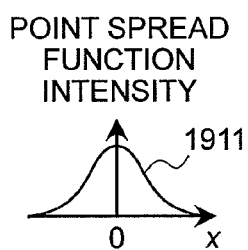 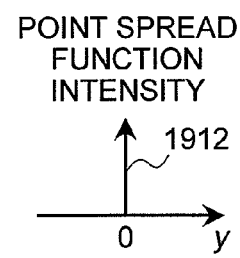

SCANNING ELECTRON MICROSCOPE AND METHOD FOR PROCESSING AN IMAGE OBTAINED BY THE SCANNING ELECTRON MICROSCOPE

CLAIM OF PRIORITY

The present application claims priority from Japanese application serial no. JP2007-009699, filed on Jan. 19, 2007, the content of which is hereby incorporated by reference into this application.

BACKGROUND OF THE INVENTION

The present invention relates to a scanning electron microscope such as a scanning ion microscope or a scanning electron microscope for scanning a specimen surface with charged particles to acquire an image and, more particularly, to a scanning electron microscope capable improving a resolving power and an S/N ratio by processing an acquired image and to an image restoring method for restoring the image acquired by the scanning electron microscope.

In order to observe a fine object clearly, there is widely utilized a scanning electron microscope having an extremely higher resolving power than that of an optical microscope. The scanning electron microscope acquires the information of a target specimen at a beam irradiated position by irradiating the target specimen with a focused electron beam and by detecting the charged particles (as may belong to a kind different from that of the irradiating charged particles) emitted from the specimen or transmitting the specimen. An enlarged image of the target specimen can be acquired by scanning the specimen with the charged particle beam.

The scanning ion microscope (as will be abbreviated into "SIM") or the scanning electron microscope (as will be abbreviated into "SEM") is well known as one scanning charged particle microscope. Especially in a semiconductor manufacturing process, the scanning charged particle microscope is used in an application not only for observing the image but also for determining the featuring quantity of the target specimen to inspect the semiconductor or to measure the pattern, thereby to detect the defect having occurred on the semiconductor wafer and inspect the cause for the defect and to measure the size and shape of the pattern. As the pattern has become the more minute, the necessity for inspecting the minute defect or for measuring the pattern highly precisely becomes the higher, and it becomes important to acquire an image of a high resolving power.

However, even any scanning charged particle microscope has a limit in the resolving power. Due to the diffraction aberration to be caused by the wave motion property of the particle and the chromatic aberration and the spherical aberration to be caused by the characteristics of a lens, the charged particle beam (such as an ion beam or an electron beam) is incident on the specimen surface with the intensity distribution of the beam diverged by those aberrations. Moreover, the charged particle beam incident in the specimen is generally diffused in the specimen, and is then emitted from the specimen or passes through the specimen. These phenomena cause the deterioration of the resolving power. In the scanning charged particle microscope, moreover, as the more charged particle beams are incident, there arises the more serious problem that the specimen is damaged or that the imaging time period becomes long. As a result, the charged particle beam of a sufficient quantity cannot be incident, and the signal quantity detected is decreased to make the S/N ratio of the taken image lower in the scanning charged particle microscope than in the optical microscope.

On the other hand, an image restoration is known as the image processing for making it possible to improve the resolution and the S/N ratio of the image. The image, as obtained by a device such as a camera, a telescope or a microscope, never fails to have a deterioration of the resolving power and a superposition of noises. The image restoration is a process for estimating a clear image of a high S/N ratio (as will be called the "ideal image"), which is prepared by eliminating the deterioration of the resolving power and the noises from those images. In the ordinary image restoration, the image, which is deteriorated in the resolving power by convoluting the point spread function indicating the resolving power deterioration degree of the ideal image and in which the image having the superposed noises is modeled as the taken image, and this model is used to estimate the ideal image reversely from the taken image. In connection with the image restoration, many researches have been performed on an astronomical image or an optical image (as referred to A. K. Katsaggelos: Optical Engineering, 28, 7, pp. 735-748 (1989), or M. R. Banham and A. K. Katsaggelos: IEEE Signal Processing Magazine, pp. 24-41 (March 1997), for example).

In the scanning optical microscope or the scanning charged particle microscope, too, a method for improving the resolving power by using the image restoration is proposed in JP-A-3-44613 or Y. I. Gold and A. Goldenshtein: Proc. SPIE, 3332, pp. 620-624 (1998).

Moreover, a calculating method for determining the beam intensity distribution on the specimen surface or one resolving power deterioration factor of the taken image is described in J. Orloff: Handbook of Charged Particle Optics, CRC Press (1997), for example.

In JP-A-2001-15055, moreover, it is described that the information on the side face of a specimen is obtained by irradiating the specimen obliquely with an electron beam to take an image.

SUMMARY OF THE INVENTION

In the methods proposed in Patent Document 1 and Non-Patent Document 3, however, the point spread function is exemplified by a fixed beam intensity distribution, which has the following problems.

For example, the beam intensity distribution may be seriously different according to parameters for determining the imaging condition such as an acceleration voltage, a probe current or a beam divergence angle, and is also different according to a beam tilt angle in case an image is taken by tiling the beam. Moreover, the beam intensity distribution is easily influenced by the performance of the lenses to converge the charged particle beam, and may change even if the performances of the lenses are made slightly different by the state of a device. The deterioration of the resolving power due to the beam intensity distribution cannot be sufficiently reduced, unless a proper point spread function is used according to those imaging conditions.

In case the target specimen has a sufficient height, as compared with a focal depth, for example, the beam intensity distribution is largely different according to the height of the specimen. This is because one image is ordinarily taken with the focal position being fixed so that it is focused in the case where the focal position is close to the sample surface, but goes out of focus as it becomes farther from the specimen surface. In this case, the resolving power of the region out of focus cannot be sufficiently improved, unless the point spread function is changed according to the height information of the specimen.

In order to improve the resolving power better, moreover, it is desired to reduce the resolving power deterioration factor other than the beam intensity distribution, such as the influences due to the diffusion of the charged particle beam in the specimen or the influences from the beam scan.

In the measurements of the size and shape of the semiconductor pattern, for example, a processing for preventing the fluctuations of the measurement due to the difference in the measured value between the devices and the aging of the devices is needed for realizing a stable measuring precision. The major causes for the difference and fluctuation of the measured values of this case are thought to come from the difference in the beam intensity distribution. Therefore, the concept of reducing the difference in the beam intensity distribution by performing the image restoration, using the beam intensity distribution itself as the point spread function is useful. In the case where the S/N ratio of the taken image is so low that the image restoration has to be performed for a short time period, however, it is difficult to improve the resolving power sufficiently. By using the beam intensity distribution itself as the point spread function, therefore, it is seriously difficult to reduce the difference in the beam intensity distribution sufficiently.

In order to solve the aforementioned problems, according to one aspect of the invention, there is provided a scanning electron microscope device comprising: charged particle beam irradiating optical system means for irradiating and scanning a specimen having a pattern with a focused charged particle beam; charged particle detecting optical system means for detecting the charged particles of the kind identical to or different from that of the charged particles emitted from the specimen, which was irradiated and scanned with the charged particle beam by the charged particle beam irradiating optical system means; image acquiring means for acquiring a charged particle image of the specimen by processing a signal detected by the charged particle detecting optical system means; and image processing means for processing the charged particle image of the specimen acquired by the image acquiring means, wherein the image processing means determines a restored image of the image, which is acquired by the image acquiring means, by using a point spread function calculated by using imaging information containing at least one of the image acquiring condition of the image acquired by the image acquiring means and the information of the taken specimen.

According to another aspect of the invention, there is provided a method for processing an image acquired by a scanning electron microscope device, comprising the steps of: irradiating and scanning a specimen having a pattern with a charged particle beam focused by using the scanning electron microscope device, to detect the charged particles produced from the specimen thereby to acquire the charged particle image of the specimen; and processing the charged particle image of the acquired specimen, wherein a point spread function calculated by using imaging information containing at least one of the image acquiring condition of the image acquired by the image acquiring means and the information of the taken specimen is used to determine a restored image of the acquired charged particle image.

According to the invention, a scanning charged particle microscope is enabled to observe a minute constitution and calculate the featuring quantity of a target specimen highly precisely by performing an image restoring processing, using an imaging condition, specimen information and a point spread function adapted for an application.

These and other objects, features and advantages of the invention will be apparent from the following more particular description of preferred embodiments of the invention, as illustrated in the accompanying drawings.

BRIEF DESCRIPTION OF THE DRAWINGS

FIG. 10A is a diagram showing a diffusion region of a charged particle beam inside of a specimen of a weak interaction between the charged particle and the specimen, in the case where the specimen is irradiated with the charged particle, FIG. 10B is a diagram showing a diffusion region of a charged particle beam inside of a specimen of a strong interaction between the charged particle and the specimen, in the case where the specimen is irradiated with the charged particle, the diffusion region being different depending on the shape of the specimen in the vicinity of the beam irradiation position, and FIG. 10C is a diagram showing a diffusion region of a charged particle beam inside of a specimen having a step, in the case where the specimen is irradiated with the charged particle;

FIG. 11A is a diagram schematically showing the state, in which the specimen is irradiated with a charged particle beam, FIG. 11B is a diagram showing the characteristics in the x-direction of a point spread function to be created according to a beam scanning rate for an image restoration, and FIG. 11C is a diagram showing the characteristics in the y-direction of the point spread function to be created according to the beam scanning rate for an image restoration;

DESCRIPTION OF THE PREFERRED EMBODIMENTS

Embodiments according to the invention are described with reference to the accompanying drawings.

[Description of Image Restoration Principle]

In order to improve a resolving power and an S/N ration of a taken image, the invention performs an image restoration by using a proper point spread function. The principle of the image restoration according to the invention is described in the following.

Figure 1:
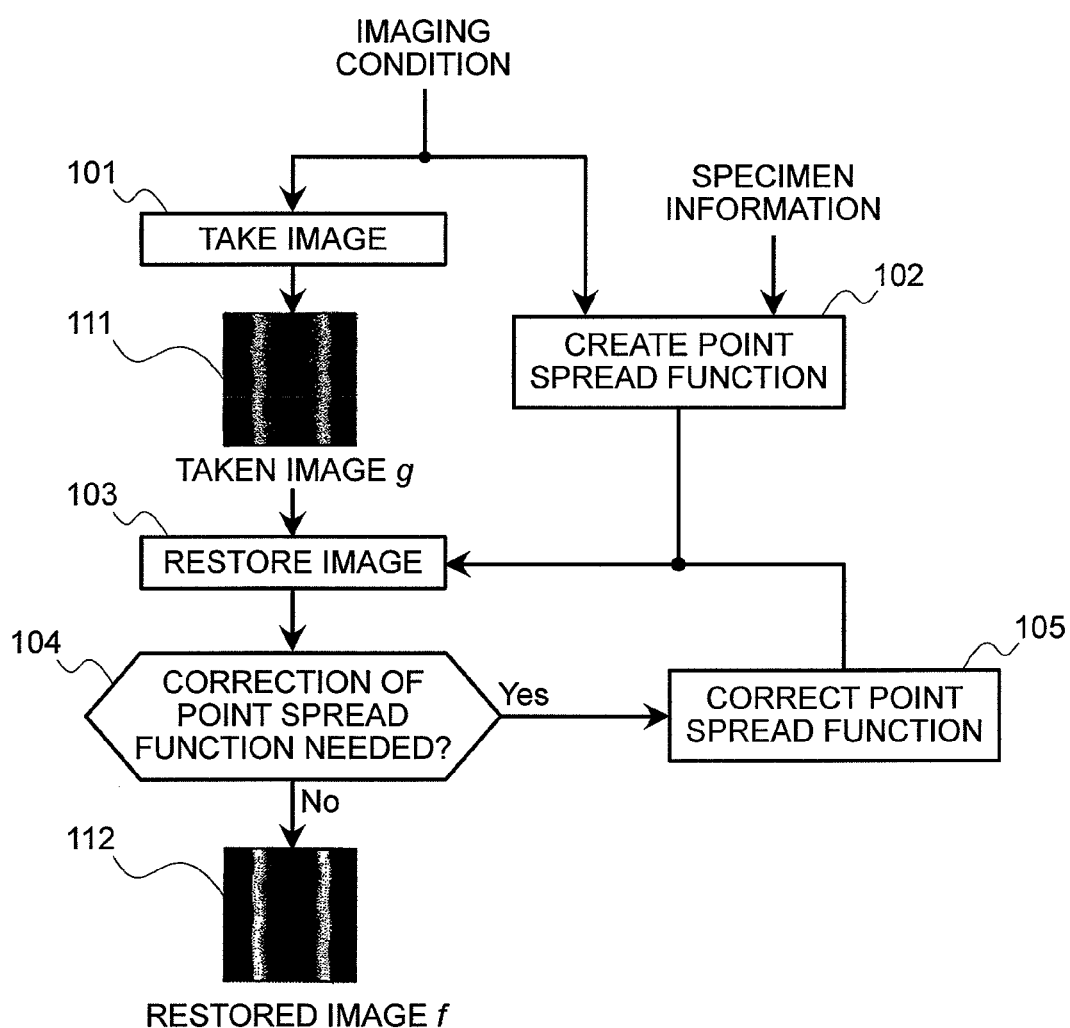
FIG. 1 shows one embodiment of a sequence of performing an image restoration by taking an image.

FIG. 1 shows one embodiment of a sequence of performing an image restoration by taking an image. At first, under a preset imaging condition, an imaging operation is performed at Step 101 to acquire a taken image g at 111. The imaging condition is exemplified by a device kind indicating information on the device, a device ID, a device state, and an imaging parameter such as an acceleration voltage, a probe current, a beam divergence angle, a beam tilt angle or a focal position. At Step 102, a point spread function A is created on the basis of that imaging condition and specimen information.

Next at Step 103, the image restoration is performed to determine a restored image f at 112. Moreover, a function for the user to correct the point spread function may be added, as indicated at Steps 104 and 105. At Step 104, the user is asked whether or not the point spread function has to be corrected. In the case where the answer is Yes, the point spread function corrected at Step 105 is used to perform the image restoration at Step 103, and this image restoration is repeated till the point spread function need not be corrected.

In the case where the image is consecutively taken, the operations of Steps 104 and 105 may be performed on the firstly taken image but are not ordinarily performed on the second and subsequent images.

Figure 2:
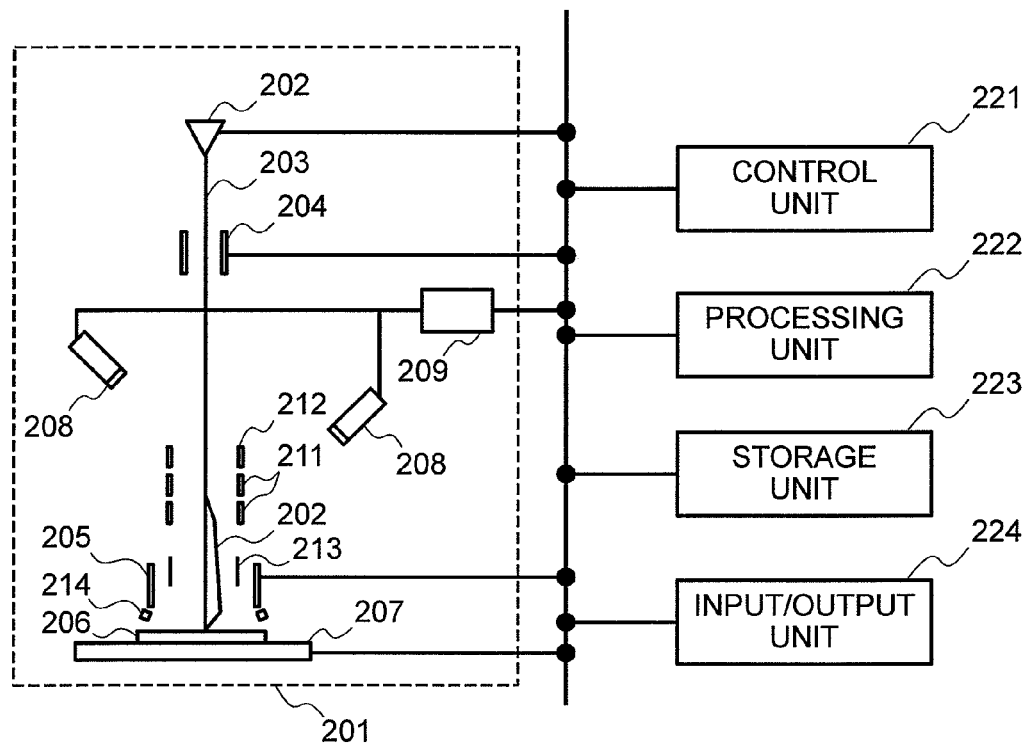
FIG. 2 shows a basic constitution of the SEM according to one mode of embodiment of the invention.
Figure 3A:
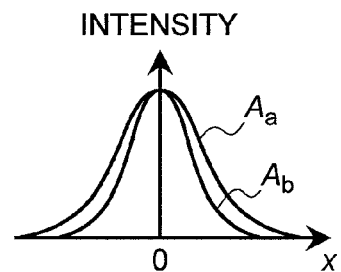
FIG. 3A and FIG. 3B show examples of point spread functions for reducing the difference in a resolving power between two point spread models.
Figure 3B:
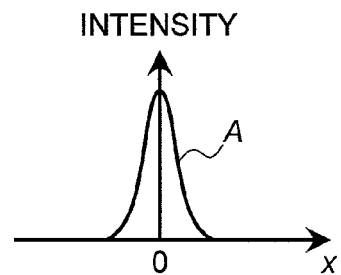

FIG. 2 shows a basic constitution of the SEM according to one mode of embodiment of the invention. For example, the SEM is constituted to include an imaging device 201, a control unit 221, a processing unit 222, a storage unit 223 and an input/output unit 224. For acquiring the taken image, a primary electron beam 203 is generated from an electron gun 202 and passed through a condenser lens 204 and further through an objective lens 205 so that it is focused on the surface of a specimen 206.

Next, the taken image is acquired by detecting an electron such as a secondary electron generated from the specimen 206 or a reflected electron by a detector 208 and by generating a digital image from the detected signal by an image producer 209.

The taken image is stored in the storage unit 223. By moving a stage 207, the image can be taken at an arbitrary position of the specimen. The detector 208 may also be exemplified by a plurality of detectors such as a secondary electron detector for more detecting secondary electrons and a reflected electron detector for more detecting reflected electrons. The detector may be further exemplified by a height measuring sensor 214 for measuring the height of the specimen.

The information on the side of the specimen can be acquired when the imaging operation is performed by irradiating the specimen with a primary electron beam 210 in an oblique direction. The oblique irradiation with the electron beam is exemplified in Patent Document 2 by the method of inclining the electron beam by using a deflecting unit 211 for deflecting the electron beam off an optical axis, and a correction unit 212 for substantially correcting a chromatic aberration on the specimen surface by dispersing the electron beam.

Other than this method, the imaging operation can also be performed by irradiating the specimen with the charged particle beam in the oblique direction by a method using a plurality of columns, a method inclining the column or a method inclining the stage 207. The more obliquely the specimen is irradiated, however, the more the beam intensity distribution diverges, thereby to lower the resolving power of the taken image.

The control unit 221 controls the voltage to be applied to the periphery of the electron gun 202, the focal position adjustments of the condenser lens 204 and the objective lens 205, the movement of the stage 207, the action timing of the image generator 209 and so on. The processing unit 222 performs the creation of the point spread function at Step 102, the image restoration at Step 103, the decision of the correction propriety of the point spread function at Step 104, the correction of the point spread function at Step 105, and so on.

The storage unit 223 stores the taken image, the restored image, the imaging condition, the specimen information and so on. The input/output unit 224 performs the input of the imaging condition, the output of the taken image or the restored image, the correction of the point spread function, and so on.

The taken image g never fails to be accompanied by a resolving power deterioration for some cause and a reduction of the S/N ratio for a noise superposition. The taken image g(x, y) can be expressed as the image, in which a noise n(x, y) is superposed on a convolution between a point spread function A(x', y') expressing the behavior of the resolving power deterioration and the restored image f(x, y):

$$g(x, y) = \sum_{x',y'} A(x', y') f(x - x', y - y') + n(x, y). \quad \text{(Formula 1)}$$

Here, the restored image f is an image having neither a resolving power deterioration by the point spread function A nor the superposition of the noise n. This noise n is frequently assumed by a white Gaussian noise independent from the restored image f, but may be a noise which is not independent of f or a noise other than the Gaussian distribution such as a noise according to a Poisson distribution.

Moreover, the noise need not be additive but may be a noise, as expressed by:

$$g(x, y) = n(x, y) \sum_{x',y'} A(x', y') f(x - x', y - y'). \quad \text{(Formula 2)}$$

The restored image f need not always be an image, from which all the resolving power deteriorating factors or all the noises are eliminated. In the case where the point spread function has two resolving power deteriorating factors expressed by $A_1(x', y')$ and $A_2(x', y')$, for example, the restored image f can be set not to have the two resolving power deteriorations by expressing the point spread function A(x', y'), as expressed by:

$$A(x', y') = \sum_{u,v} A_1(u, v) A_2(x' - u, y' - v). \quad \text{(Formula 3)}$$

Alternatively, one of the resolving power deteriorations can be exclusively reduced by expressing the point spread function A(x', y') by A(x', y')=$A_1$ ((x', y') or A(x', y')=$A_2$ (x', y').

Moreover, it is substantially impossible to eliminate the noise completely from the image. The more strongly the noise is eliminated, the wider an adverse effect can be extended by eliminating a minute constitution. In order to prevent the adverse effect, a noise of some extent can be left in the restored image f.

The resolving power deteriorating factors to be considered are the divergence of the beam intensity distribution on the specimen surface, the diffusion of the beam in the specimen, the influences of a beam scan and so on. The resolving power deteriorations due to the individual phenomena can be reduced by performing the image restoration using the point spread function matching the individual resolving power deteriorating factors.

Moreover, the point spread function need not correspond directly to those resolving power deteriorating factors. In the case where the beam intensity distribution on the specimen surface under a different imaging condition is expressed by functions $A_a$(x', y') and $A_b$(x', y'), as shown in FIG. 5, the point spread function may be exemplified by the function A(x', y') satisfying the following Formula:

$$A_a(u, v) = \sum_{x',y'} A(x', y') A_b(u - x', v - y'). \quad \text{(Formula 4)}$$

By using this point spread function, the difference in the resolving power between the two beam intensity distributions can be reduced. The function A(x', y') can be calculated by a method, in which the functions $A_a$(x', y') and $A_b$(x', y') are Fourier-transformed, in which a function $FA_a(f_x', f_y')$ is divided by a function $FA_b(f_x, f_y)$ to calculate $FA_a(f_x, f_y)/FA_b(f_x, f_y)$, and in which the result is inversely Fourier-transformed.

In the image restoration, Formula (1) is inversely solved for the given taken image g to determine the restored image f. The solution of the image restoration is exemplified by a noniterative method, in which the inverse function of the point spread function A or a function $A^+$ corresponding to the inverse function is determined to cause $A^+$ to act directly on the taken image g, or an interative method, in which a restored image f of a high resolving power is determined by repeating the operations. The noninterative method is generally advantageous in that the restored image f can be quickly determined, and the method using a Wiener filter is famous. On the other hand, the interative method can generally acquire the restored image f of a satisfactory image quality.

Figure 4:
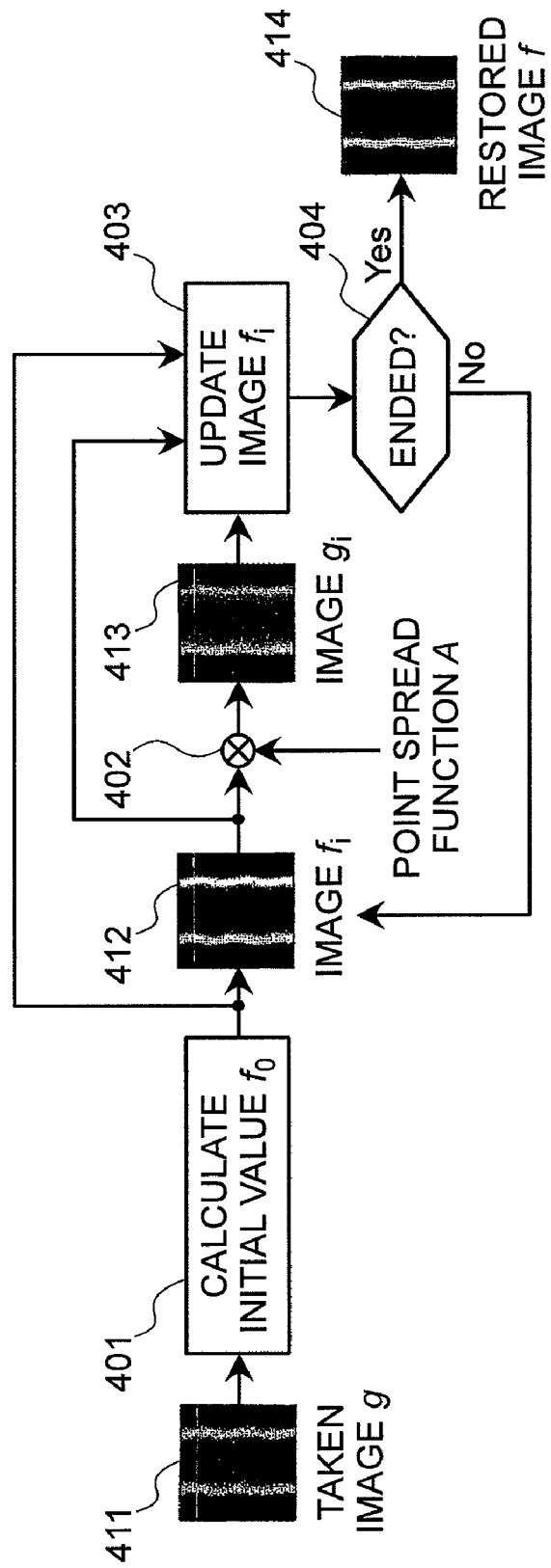
FIG. 4 shows one embodiment of an image restoration based on an iterative method.

FIG. 4 shows one embodiment of an image restoration based on an iterative method. In this iterative method, an image $f_i$ is iteratively updated to improve the resolving power of the image $f_i$ and to reduce the noise thereby to determine the restored image f. At first, an image $f_0$ or the initial value of an image $f_i$ is produced at Step 401 by using the taken image g. The image $f_0$ may be exemplified not only by the taken image g itself but also by either an image produced by subjecting the taken image g to a previous processing such as a denoising operation or a restored image determined by another image restoring method. Next, at Step 402, an image $g_0$ or a convoluted result of the image $f_0$ and the point spread function A is calculated. After this, at Step 403 of updating the image $f_i$, the image $f_0$ is updated to acquire the image $f_1$ by using the taken image g, the image $f_0$ and the image $g_0$.

Then, the operations of Steps 402 to 404 are repeated till the ending condition is satisfied at Step 404, thereby to update the image $f_i$, and this image $f_i$ is outputted as the restored image f when the ending condition is satisfied. The conceivable ending condition is after a predetermined number of repetitions were executed, after a predetermined processing time was elapsed, when the amount of updating the image $f_i$ becomes sufficiently small, when the image $f_i$ satisfied a specific condition, and so on.

Many methods have been proposed as Step 403 of updating the image $f_i$. In the Richardson-Lucy method widely known as the iterative method, for example, the image $f_i$ is updated according to the following Formula:

$$f_{i+1}(x, y) = f_i(x, y) \sum_{x',y'} A(-x', -y') \frac{g(x - x', y - y')}{g_i(x - x', y - y')}. \quad \text{(Formula 5)}$$

In this method, the image $f_i$ converges into a maximum likelihood solution when the noise accords the Poisson distribution. In another method, the image $f_i(x, y)$ is updated to reduce an evaluation function $H(f_i(x, y))$ under the following restricting condition of:

$$\sum_{x,y} |g(x, y) - g_i(x, y)|^2 = \sigma^2. \quad \text{(Formula 6)}$$

Here, letter $\sigma$ designates the standard deviation of the noise n.

Formula (6) is based on the property, in which the difference between an image $g_i$ and the taken image g becomes the noise n when the image $f_i$ is identical to the restored image f in Formula (1). This problem can be replaced by the problem of minimizing the following Formula by using the Lagrange's undetermined coefficient eta, so that the image $f_i$ can be updated by using the optimizing method such as the steepest descent method or the Newton's method.

$$J = H(f_i(x, y)) + \eta \left( \sum_{x,y} |g(x, y) - g_i(x, y)|^2 - \sigma^2 \right). \quad \text{(Formula 7)}$$

The detailed method is described in Non-Patent Document 1.

FIG. 5 shows one example of the beam intensity distribution on the specimen surface or one resolving power deterioration cause of the taken image. In FIG. 5A, both beams 301 and 302 at (1) and (2) have some width, and are so converged on the surface of a specimen 303 as to go with narrow widths. The beam 301 at (1) is incident in a direction perpendicular to an x-axis and a y-axis. On the other hand, the beam 302 at (2) of FIG. 5A is perpendicular to the y-axis but is tilted at the beam tilt angle $\theta$ with respect to the x-axis.

Figure 5A:
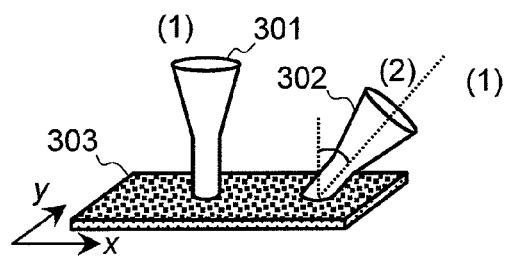
FIG. 5A is a perspective view showing an electron beam vertically incident on a specimen and an electron beam incident at a beam tilt angle θ.
Figure 5B:
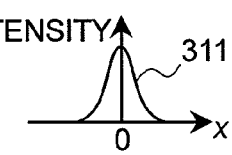
FIG. 5B shows one example of a beam intensity distribution in an x-direction of an electron beam 301 vertically incident on the specimen.
Figure 5C:
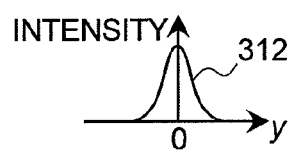
FIG. 5C shows one example of a beam intensity distribution in a y-direction of the electron beam 301 vertically incident on the specimen.
Figure 5D:
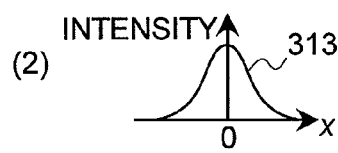
FIG. 5D shows one example of a beam intensity distribution in the x-direction of an electron beam 302 incident at the beam tilt angle θ on the specimen.
Figure 5E:
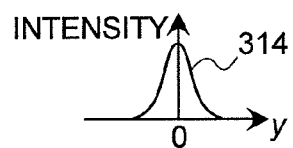
FIG. 5E shows one example of a beam intensity distribution in the y-direction of the electron beam 302 incident at the beam tilt angle θ on the specimen.

The beam intensity distributions of the beams 301 and 302 on the specimen surface (assumed to be parallel to the xy-plane) are shown in FIG. 5B to 5E. If all the properties other than the directions of incidence of the beams 301 and 302 are identical, the beam intensity distributions with respect to the y-direction, as shown in FIG. 5C and FIG. 5E, that is, a distribution 312 of FIG. 5C and a distribution 314 of FIG. 5E can be deemed as identical. When the beam intensity distributions with respect to the x-direction, that is, a distribution 311 of FIG. 5B and a distribution 313 of FIG. 5D are compared, on the other hand, the obliquely incident beam 302 becomes more divergent.

As the beam intensity distribution on the specimen surface becomes more divergent, the resolving power deterioration is more caused, so that the resolving power ordinarily more deteriorates as the beam tilt angle $\theta$ becomes larger.

In the case where another condition is different, the beam intensity distribution takes another shape. The value indicating the extension of the beam intensity distribution is exemplified by the diffraction aberration $d_d$ caused by the property as a wave owned by the charged particle, and the chromatic aberration $d_c$ and the spherical aberration $d_s$ or the lens characteristics. The individual aberrations $d_d$, $d_c$ and $d_s$ are expressed by the following Formulas, respectively:

$$d_d = \frac{0.61\lambda}{\sin\alpha}; \quad \text{(Formula 8)}$$

-continued $$d_c = C_c \alpha \frac{\Delta \Phi}{\Phi}; \quad \text{(Formula 9)}$$

and $$d_s = C_s \frac{\alpha^3}{2}. \quad \text{(Formula 10)}$$

Here: $\lambda$ designates the de Broglie wavelength; $\alpha$ a beam divergence angle on the specimen surface; $\Phi$ an acceleration voltage of the charged particle beam; $\Delta \Phi$ a fluctuation of the acceleration voltage $\Phi$; $C_c$ a chromatic aberration coefficient; and $C_s$ a spherical aberration coefficient.

Figure 6A:
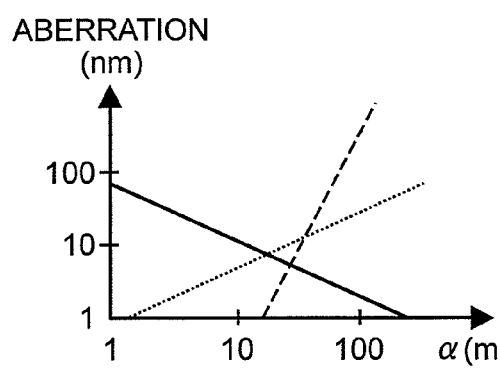
FIG. 6A is a graph showing relations between a diffraction aberration dd, a chromatic aberration dc and a spherical aberration ds, and a beam divergence angle.
Figure 6B:
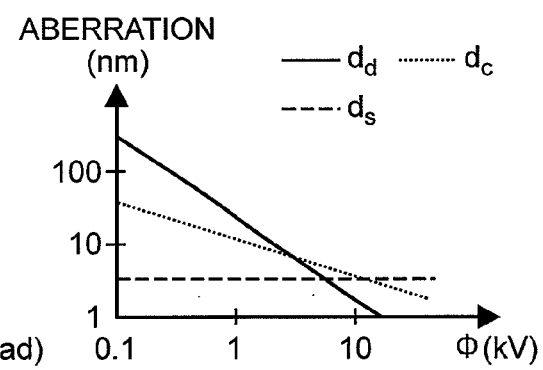
FIG. 6B is a graph showing relations between the diffraction aberration dd, the chromatic aberration dc and the spherical aberration ds, and an acceleration voltage.

FIG. 6A shows, as one example of those aberrations changing with the imaging condition, relations between the beam divergence angle $\alpha$ and the individual aberrations $d_d$, $d_c$ and $d_s$ of the case, in which the chromatic aberration coefficient $C_c$ and the spherical aberration coefficient $C_s$ are constant, and the relations between the acceleration voltage $\Phi$ and the individual aberrations $d_d$, $d_c$ and $d_s$. Here, the reason why the diffraction aberration $d_d$ is changed by the acceleration voltage $\Phi$ in FIG. 6B is that the de Broglie wavelength $\lambda$ of the charged particle is proportional to −½ power of the acceleration voltage $\Phi$. The chromatic aberration coefficient $C_c$ and the spherical aberration coefficient $C_s$ are values expressing the characteristics of the lens for focusing the charged particle beam, and are ordinarily changed by the acceleration voltage $\Phi$, the beam divergence angle $\alpha$ and so on.

The beam intensity distribution can be either approximately determined by using the individual aberrations $d_d$, $d_c$ and $d_s$ or precisely by the calculating method, as described in Non-Patent Document 4, for example. Alternatively, the beam intensity distribution can also be estimated by performing the measurements for every conditions. The beam intensity distribution is also changed by those conditions, as the aberrations are changed with the acceleration voltage $\Phi$ and the beam divergence angle $\alpha$. On the other hand, the beam intensity distribution is also changed by the electric current (or the probe current) of the charged particle beam, the focal position or the like. In the case where the resolving power deterioration cause by the beam intensity distribution is contained in the point spread function, therefore, the point spread function suitable for the imaging condition, such as the acceleration voltage $\Phi$, the beam divergence angle $\alpha$, the probe current or the focal position has to be used for performing the image restoration properly.

Figure 7:
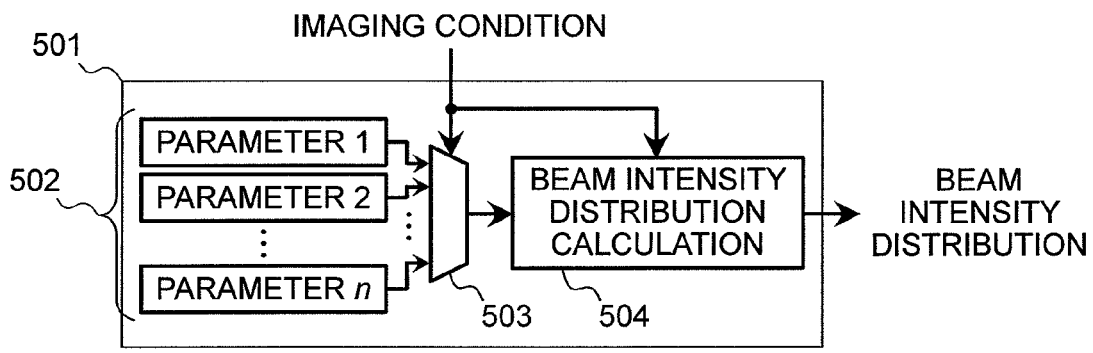
FIG. 7 shows one embodiment of a step of calculating a beam intensity distribution in accordance with an imaging condition.

FIG. 7 shows one embodiment of a step of calculating a beam intensity distribution in accordance with an imaging condition. In the case where the image restoration is performed by using the beam intensity distribution as the point spread function, the step 501 of calculating the beam intensity distribution can be utilized as Step 102 of FIG. 1 of creating the point spread function. The parameter, as changed according to the imaging condition, necessary for calculating the beam intensity distribution is stored in advance as 502 for a plurality of imaging conditions. The parameters 502 are exemplified by the chromatic aberration coefficient $C_c$, the spherical aberration coefficient $C_s$ and so on. Next, a selection is made for a parameter matching the imaging condition given by a switch 503. After this parameter selection, the beam intensity distributions according to those imaging conditions are calculated by a beam intensity distribution calculation 504. In the case where the parameters of the imaging conditions completely identical to the given imaging conditions are not stored at 502, the switch 503 may either select the parameter in the imaging condition the closest to the given imaging condition or estimate by using the parameters matching the plurality of imaging conditions close to the given imaging condition.

Figure 8:
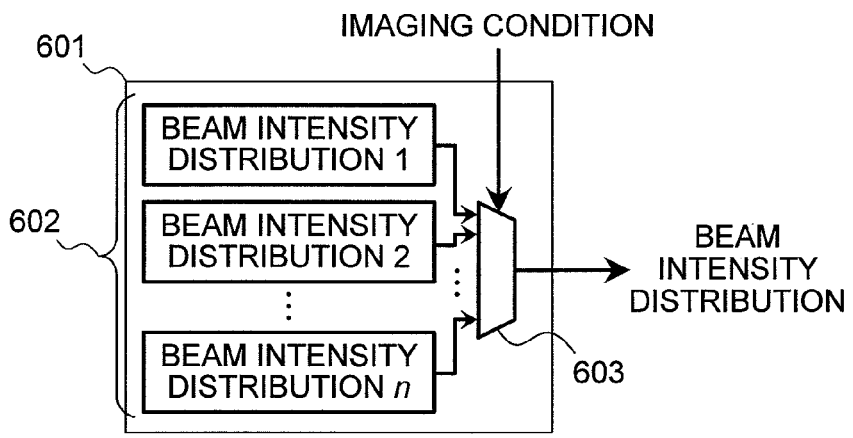
FIG. 8 shows one embodiment of a step of calculating a beam intensity distribution in accordance with an imaging condition.

FIG. 8 shows another embodiment of a step of calculating a beam intensity distribution in accordance with an imaging condition. The beam intensity distributions for the imaging conditions are stored in advance at 602. Next, a selection is made on the beam intensity distribution matching the imaging condition given by a switch 603. In the case where the parameters of the imaging conditions completely identical to the given imaging conditions are not stored at 602, the switch 603 may either select the beam intensity distribution in the imaging condition the closest to the given imaging condition or interpolate the beam intensity distribution in the imaging conditions close to the given imaging condition.

Figure 9A:
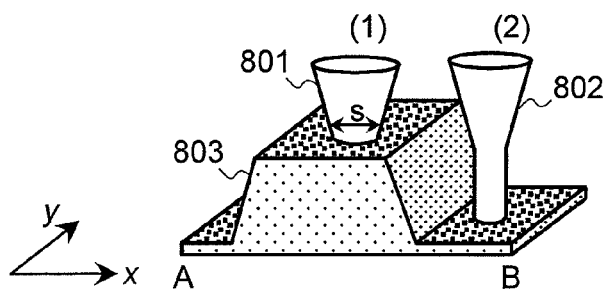
FIG. 9A is a schematic perspective view of a specimen of a large height difference and shows the state, in which the specimen is irradiated with a charged particle beam.
Figure 9B:
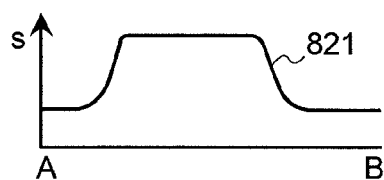
FIG. 9B is a diagram showing a relation between an irradiation position and a beam diameter (S) at the time when the specimen of a large height difference of FIG. 9A is scanned with the charged particle beam.
Figure 9C:
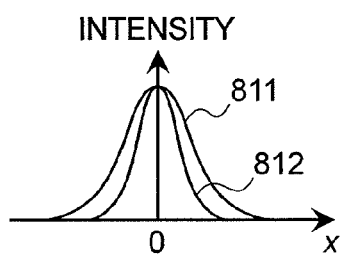
FIG. 9C is a diagram showing abeam intensity distribution (812) of a charged particle in focus on the specimen surface and a beam intensity distribution (811) of the charged particle out of focus.

The specimen information may be needed for the calculation of the point spread function. FIG. 9A to FIG. 9C show the behaviors of the case, in which a specimen of a large height difference is irradiated with a charged particle beam. In FIG. 9A, a charged particle beam 802 is focused on the surface of a specimen 803, and its beam intensity distribution is not diverged so much, as indicated at 812. On the other hand, a charged particle beam 801 is out of focus on the surface of the specimen 803, and its beam intensity distribution is more divergent, as indicated at 811 in FIG. 9C, than the beam intensity distribution 812. The specimen 803, which has a large height difference for the focal depth of the charged particle beam, may go out of focus, as indicated by the charged particle beam 801. In this case, the beam diameter s of the charged particle beam changes with the beam irradiation position, as indicated at 821 in FIG. 9B. This change acquires the taken images having different resolving powers for positions. In order that the resolving power deterioration by the beam intensity distribution may be properly reduced for that image, it is necessary to determine the beam intensity distribution of each beam irradiation position (x, y) by using the shape of the specimen, especially the information on the height of the specimen and the focal position, thereby to determine the beam intensity distribution as the point spread function A. Here, in the case where the point spread function A changed with the beam irradiation position (x, y) is used, the point spread function is expressed by A(x', y'; x, y), so that the resolving power deterioration model of the taken image g (x, y) is expressed by the following Formula:

$$g(x, y) = \sum_{x',y'} A(x', y'; x, y) f(x - x', y - y') + n(x, y). \quad \text{(Formula 11)}$$

The height of the specimen may be measured with the height measuring sensor 214 or the like, as shown in FIG. 2, or may utilize the specimen height measured by a scanning probe microscope or the like. In the case where the specimen is the semiconductor pattern, it is also possible to utilize the pattern designing CAD (Computer Aided Design) data or the like.

FIGS. 9A to 9C show the example, in which the point spread function changes with the specimen height. In another example having the point spread function changed with the specimen information, the diffusion of the charged particle beam in the specimen may be contained in the point spread function.

FIGS. 10A to 10C are diagrams showing examples of diffusion regions of the charged particle beam inside of the specimen. The diffusion is caused by the interactions between the charged particle and the specimen, and the interactions are different for the materials of the specimens. Therefore, the width of the diffusion region is different for the material of the specimen. Even if the specimens are irradiated with an identical charged particle beam (901), the diffusion region is narrow as at 911 in a specimen 921 having a weak interaction between the charged particle and the specimen, as shown in FIG. 10A. On the other hand, the diffusion region may be wider as at 912 in a specimen 922 having a strong interaction between the charged particle and the specimen, as shown in FIG. 10B. The diffusion region of each specimen can be calculated by a Monte Carlo simulator or the like for calculating the orbit of the charged particle in the specimen. Moreover, the diffusion region is different for the shape of the specimen in the vicinity of the beam irradiation position. In the case where a step exists as at a specimen 923, as shown in FIG. 10C, for example, the diffusion region in the vicinity of the step takes a shape different from that of the diffusion region at the position having no step nearby.

In order to minimize the resolving power deterioration due to the diffusion of the charged particle beam, therefore, the point spread function has to be calculated on the basis of the shape and material of the specimen. The shape of the specimen may be measured either by using the height measuring sensor 214 or the like, as shown in FIG. 2, for example, or by using the scanning probe microscope or the like, in the case where the specimen is the semiconductor pattern, on the other hand, its shape may be acquired from the pattern designing CAD data. The material of the specimen may be acquired either with an EDX (Energy Dispersion X-ray spectrum) or the like for examining the composition of a defect, for example, or from the pattern designing CAD data, in the case where the specimen is the semiconductor pattern.

Another cause for the resolving power deterioration is exemplified by a deterioration relating to the scan of the beam. In a scanning electron microscope, either the charged particle beam emitted toward a specimen 1903, as shown in FIG. 11A, from the specimen or the charged particle transmitting the specimen, is detected while being scanned in one direction (or the x-direction), as indicated at 1901. The number of the charged particles is detected for each pixel 1902 while being changed in the beam irradiation position. However, the scan is performed during the detection so that the value obtained is smoothed in the scanning direction or the x-direction. The value is more smoothed in the x-direction, as the scanning time period per pixel becomes shorter than the response time of the detector. In order to reduce the resolving power deterioration causes, the point spread function is created to have the characteristics indicated at 1911 in FIG. 11B in the x-direction, the characteristics indicated at 1912 indicated at 1912 in FIG. 11C in the y-direction and the width only in the x-direction, in accordance with the beam scanning rate, so that the image restoration can be made by using that point spread function.

Figure 12:
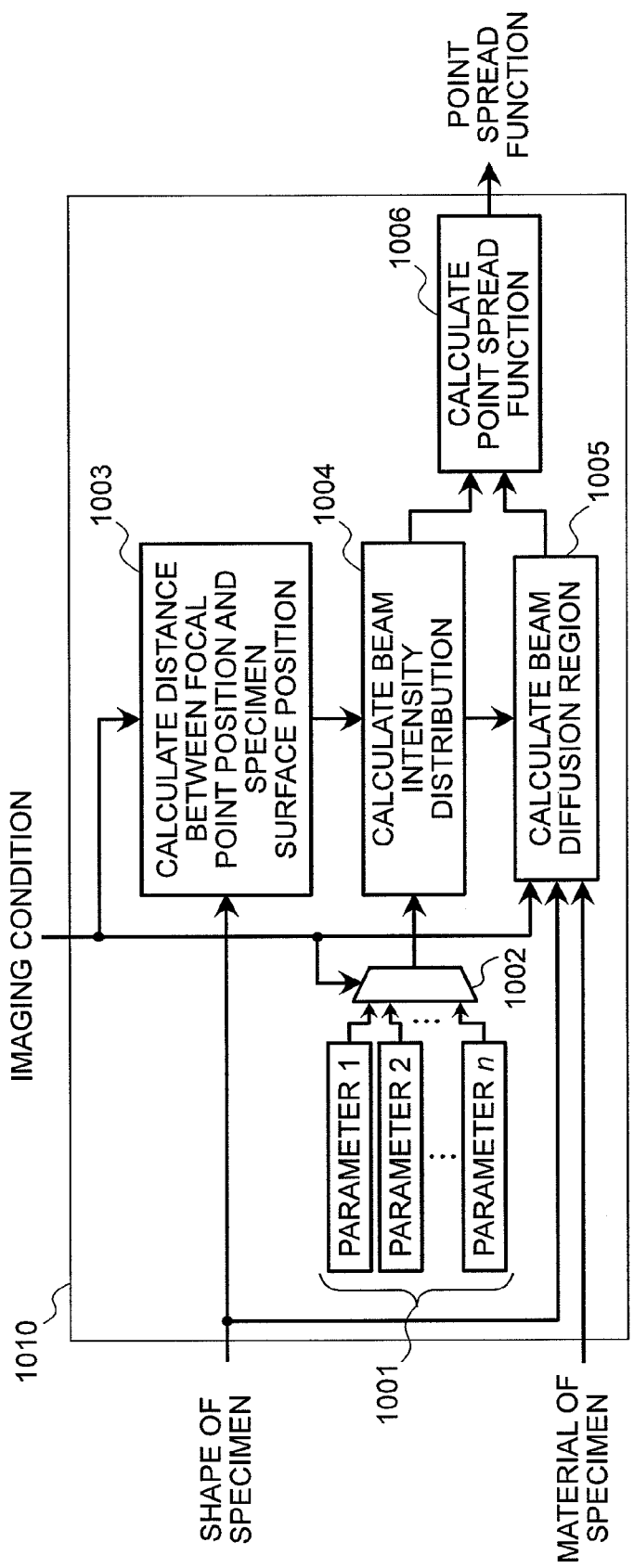
FIG. 12 shows one embodiment of a step of calculating a point spread function for reducing the deterioration of a resolving power due to a beam intensity distribution and the deterioration of the resolving power due to a diffusion of the charged particle beam in the specimen.

FIG. 12 shows one embodiment of a step of calculating a point spread function for reducing the deterioration of a resolving power due to a beam intensity distribution and the deterioration of the resolving power due to a diffusion of the charged particle beam in the specimen. At first, parameters necessary for calculating the beam intensity distribution for the imaging conditions are stored in advance, as at 1001. Next, the parameter matching the given imaging condition is selected by a switch 1002. From imaging condition and the shape of the specimen, moreover, the distance between the focal position and the specimen surface position is calculated at Step 1003.

Next, on the basis of that distance and the parameter outputted from the switch 1002, the beam intensity distribution is calculated at Step 1004. Next, the beam intensity distribution and the imaging condition, and the shape and material of the specimen are used to calculate the diffusion region of the charged particle beam in the specimen at Step 1005. At last, that beam intensity distribution and that diffusion region are used to determine the point spread function at Step 1006. In the case where the beam intensity distribution need not be calculated according to the shape of the specimen, the operation of Step 1003 can be dispensed with. In the case where the resolving power deterioration due to the beam intensity distribution is not reduced, on the other hand, the operations of Steps 1002 to 1004 can be dispensed with.

Figure 13:
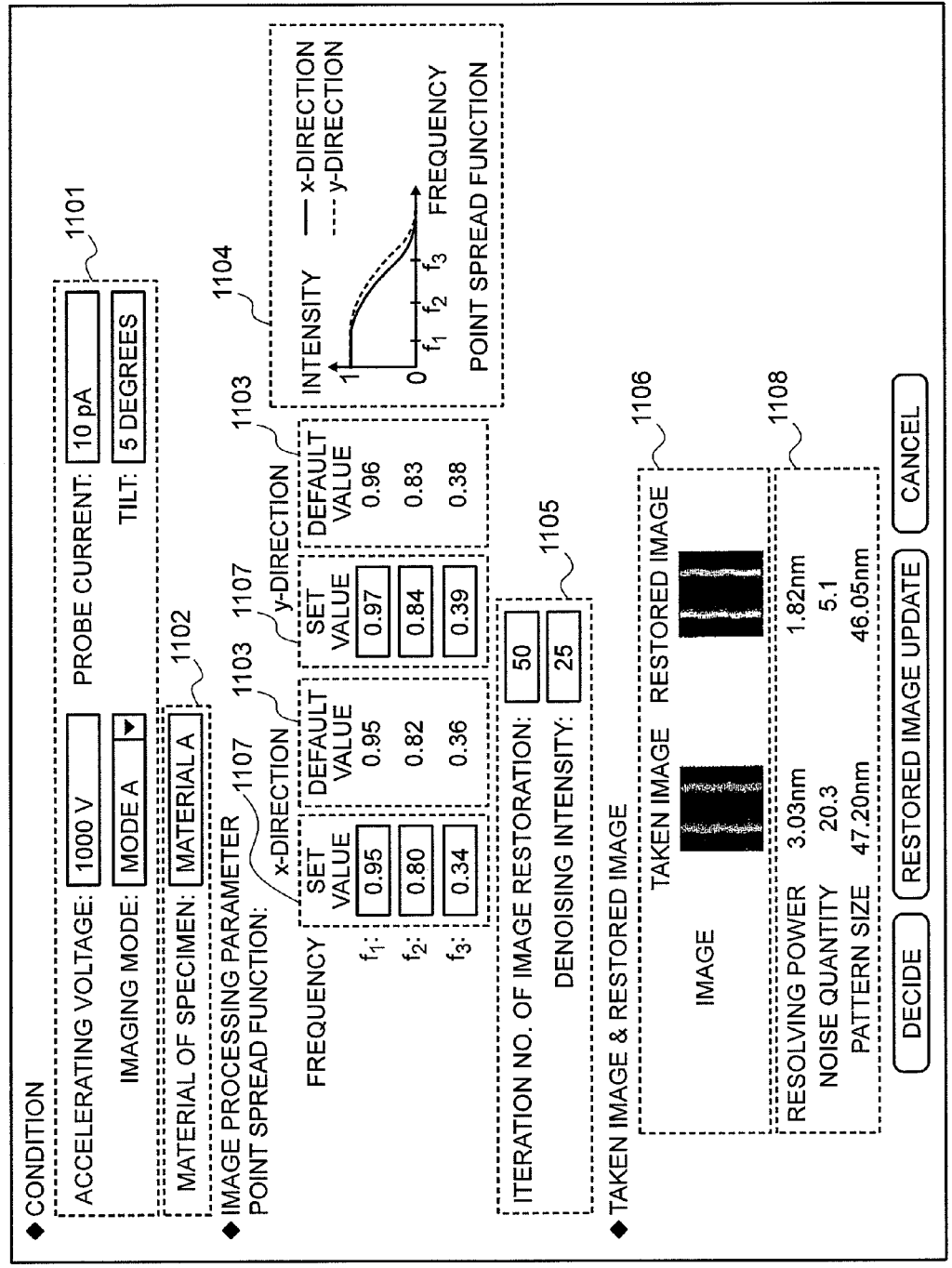
FIG. 13 shows one embodiment of a GUI screen for urging a user a method for correcting the point spread function.

In order to set the point spread function finely, there is considered the case, in which the point spread function needs to be corrected, as at Step 105 in FIG. 1, after it was created. FIG. 13 shows one embodiment of a GUI screen for urging a user a method for correcting the point spread function. This GUI screen is provided for setting the beam intensity distribution and the point spread function for reducing the resolving power deterioration due to the diffusion of the charged particle beam in the specimen.

For the given imaging condition 1101, there are the region 1104 for displaying the point spread function, the region 1103 for displaying the default value of the parameters expressing that point spread function, and a region 1107 for setting the parameter expressing that point spread function. The parameter expressing that point spread function may be exemplified by the values at several positions (x', y') of the point spread function $A(x', y')$, or the values at the several frequencies $(f_x', f_y')$ of the function $F_A(f_x', f_y')$, which was Fourier-transformed from the point spread function $A(x', y')$. Alternatively, the parameter may be one to be employed for calculating the point spread function such as the chromatic aberration coefficient $C_c$ or the spherical aberration coefficient $C_s$.

In the region 1104, there may be displayed either only the point spread function matching the parameter set in the region 1107, or the point spread function matching the default value of the parameter displayed in the region 1103. As at the region 1101, the imaging condition may also be set from the GUI screen of FIG. 13.

Like the region 1106 in the GUI screen of FIG. 13, moreover, there is a region for displaying the taken image or the restored image which is obtained by performing the image restoration, using the point spread function matching the parameter set in the region 1107. Like a region 1108, moreover, there may be a region for displaying the values which can be calculated from the individual images, such as the resolving power, the noise quantity or the pattern size. In the regions 1106 and 1108, there may also be displayed the results of the image restoration using the point spread function matching the parameters of the default, as displayed in the region 1103. There may be the region 1102 for setting the specimen information necessary for calculating the point spread function, or the region 1105 for setting the processing parameter for the image restoration. These display region and setting region may also be displayed separately of each other by using a plurality of GUI screens.

Embodiment 1

Embodiments of the case, in which the image restoration principle thus far described is applied to the defect review SEM, are described in the following.

Figure 14:
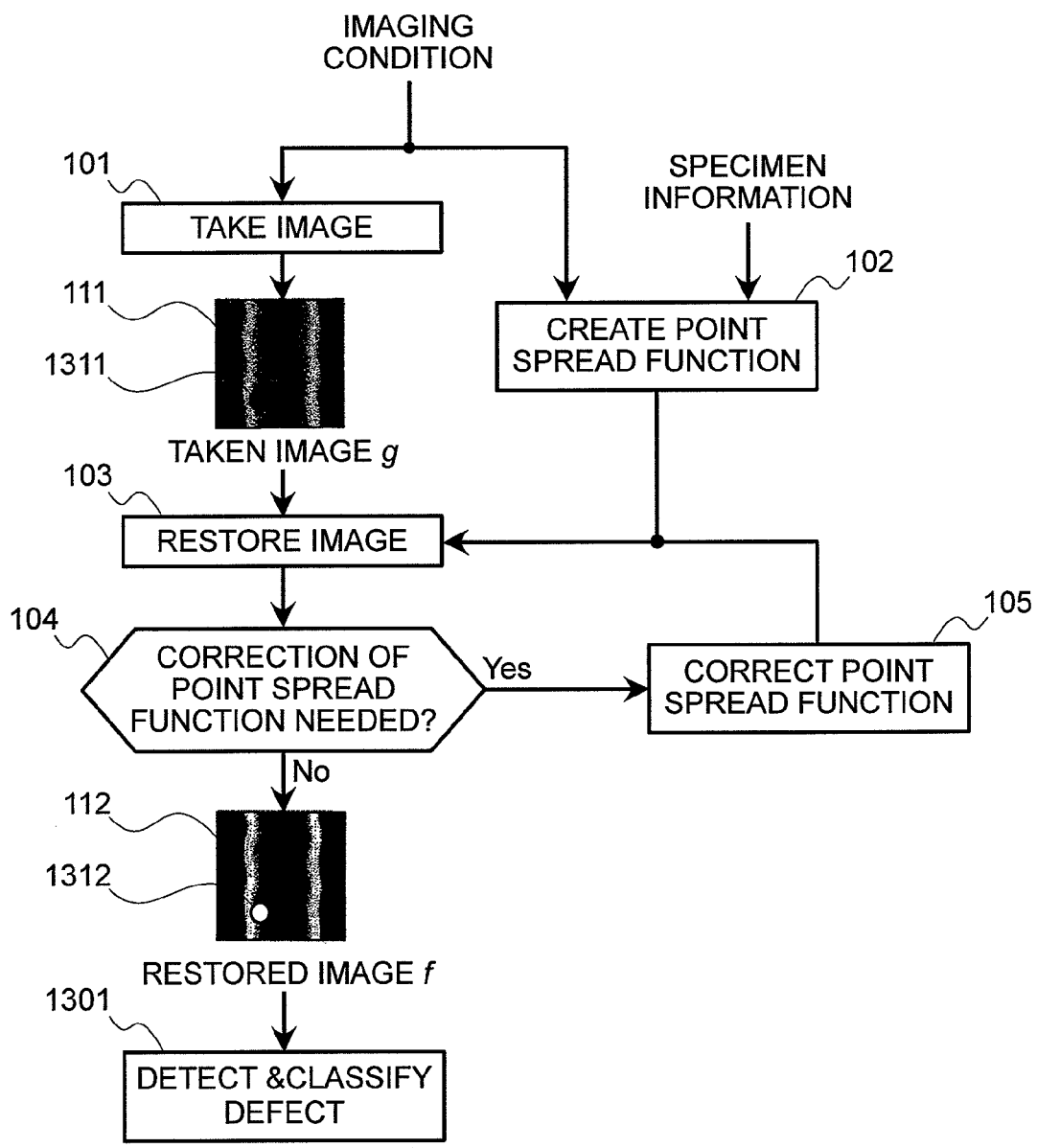
FIG. 14 shows one embodiment of a sequence of performing a defect detection or a defect classification by using a restored image obtained by an image restoration, in a semiconductor inspecting SEM such as an SEM inspecting device or a defect review SEM.

The restored image, which has been restored to a high resolving power or a high S/N ratio, can also be employed for observing a minute constitution or a high-precision measurement. FIG. 14 shows one embodiment of a sequence of performing a defect detection or a defect classification by using a restored image obtained by an image restoration in the semiconductor inspecting SEM such as the SEM inspecting device or the defect review SEM. Steps 101 to 105 are identical to those of Steps described with reference to FIG. 1. The restored image 112 is subjected to the detection of a defect or the classification into the defect kind at Step 1301. In the case where the defect detection is made on the taken image of the prior art, the taken image of a low resolving power or a low S/N ratio may be unable to be detected of its defect, even if the image contains a defect of a low contrast or a minute defect like a defect 1311. By performing the image restoration, on the contrary, a defect such as a defect 1312 can be made apparent so that it can be detected at Step 1301. In the case where the defect classification is performed at Step 1301, the classification precision can be improved for the similar reason.

Figure 15:
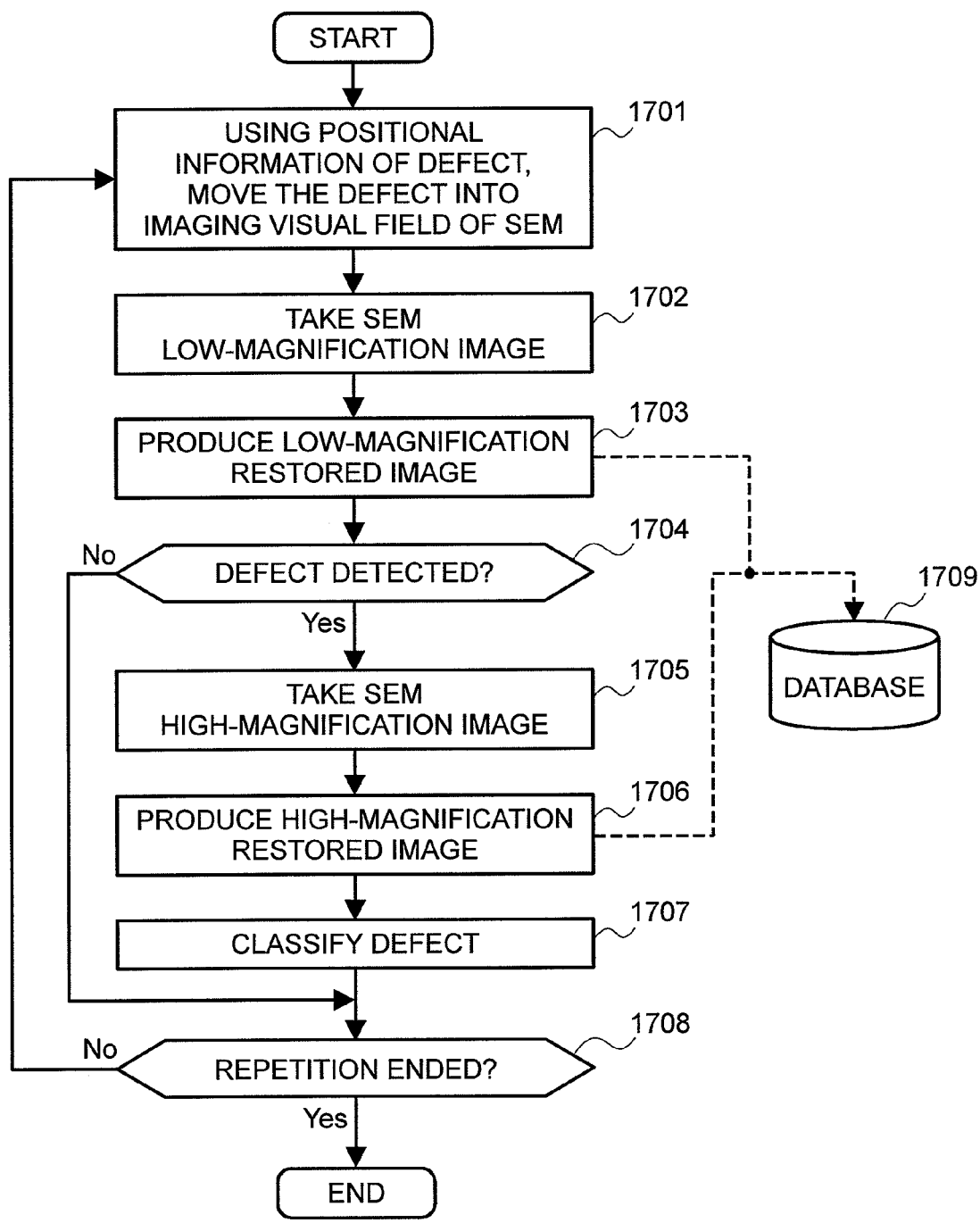
FIG. 15 shows an example of a sequence of automatically taking and classifying a defective image in the defect review SEM.

The operation of Step 1301 is specified in FIG. 15 by an example of a sequence of automatically taking and classifying a defective image in the defect review SEM. In the case where the defective image is automatically taken by the defective review SEM, the defect detection and the defect position are measured by using the various optical defect inspecting devices, as described in advance in JP-A-2-170279, JP-A-2000-105203 or JP-A-2001-255278, an optical microscope contained in the review SEM, as described in JP-A-2006-261162, and are then observed in detail by using that measured defect position information. That defect position is so low in the positional precision as is insufficient for taking an image of a high magnification directly by the review SEM. In this case, the positional information of the defect, which has been detected beforehand by the optical type defect inspecting device or the review SEM optical microscope, is used to drive the table placing the specimen thereon thereby to move the table into the observing visual field of the SEM at Step 1701.

Next, an SEM low-magnitude image is taken at Step 1702, and the taken low-magnitude image is used to perform a defect detection at Step 1704 thereby to acquire sufficient defect positional coordinates for taking high-magnitude image. At this time, in order to improve the performance of the defect detection, the low-magnitude image taken is subjected to an image restoration to produce a restored image at Step 1703, so that the restored image can be used to perform the defect detection.

In the case where a defect is to be detected at the repetition pattern such as a memory unit, moreover, the low-magnitude image of the imaged pattern containing no defect is stored and used as a low-magnitude reference image. At the defect detecting time, the low-magnitude reference image stored and an image obtained by imaging it every time and containing a low-magnitude defect are compared to detect the defect, so that the step of imaging the low-magnitude reference image every time can be omitted to make the defect detection efficient. This low-magnitude reference image stored is subjected to the aforementioned image restoration, so that the image having its noise component reduced can be used as the low-magnitude reference image. As a result, the defect can be more precisely detected by determining the differential image between that low-magnitude reference image and the aforementioned restored image containing the low-magnitude defect.

Next, in the case where the defect is detected at Step 1704 of the defect detection, the positional coordinates of the detected defect on the SEM are registered. An SEM high-magnitude image is taken in those registered defect positional coordinates at Step 1705, and the defect kinds are classified at Step 1707 by using the high-magnitude image. At this time, in order to perform the defect classification of Step 1707 highly efficiently, the high-magnitude image obtained is restored at Step 1706, and the defect classification is performed by the restored image obtained. At Step 1708, it is decided whether or not all the defect detections were ended. If not, the operations of Steps 1701 to 1707 are repeated for every target defects. The image restoration of either Step 1703 or Step 1706 can be omitted. The restored image produced at Step 1706 is stored in a database 1709. Moreover, the restored image produced at Step 1703 can also be stored in the database 1709.

According to this embodiment, a more minute defect can be observed by using the denoised image. Moreover, a clearer image can be attained so that the featuring quantity of the defect can be determined more precisely thereby to improve the classification precision of the detected defect.

Embodiment 2

Here is described an embodiment of the case, in which the aforementioned image restoration principle is applied to the semiconductor measuring SEM such as the measuring SEM.

Figure 16:
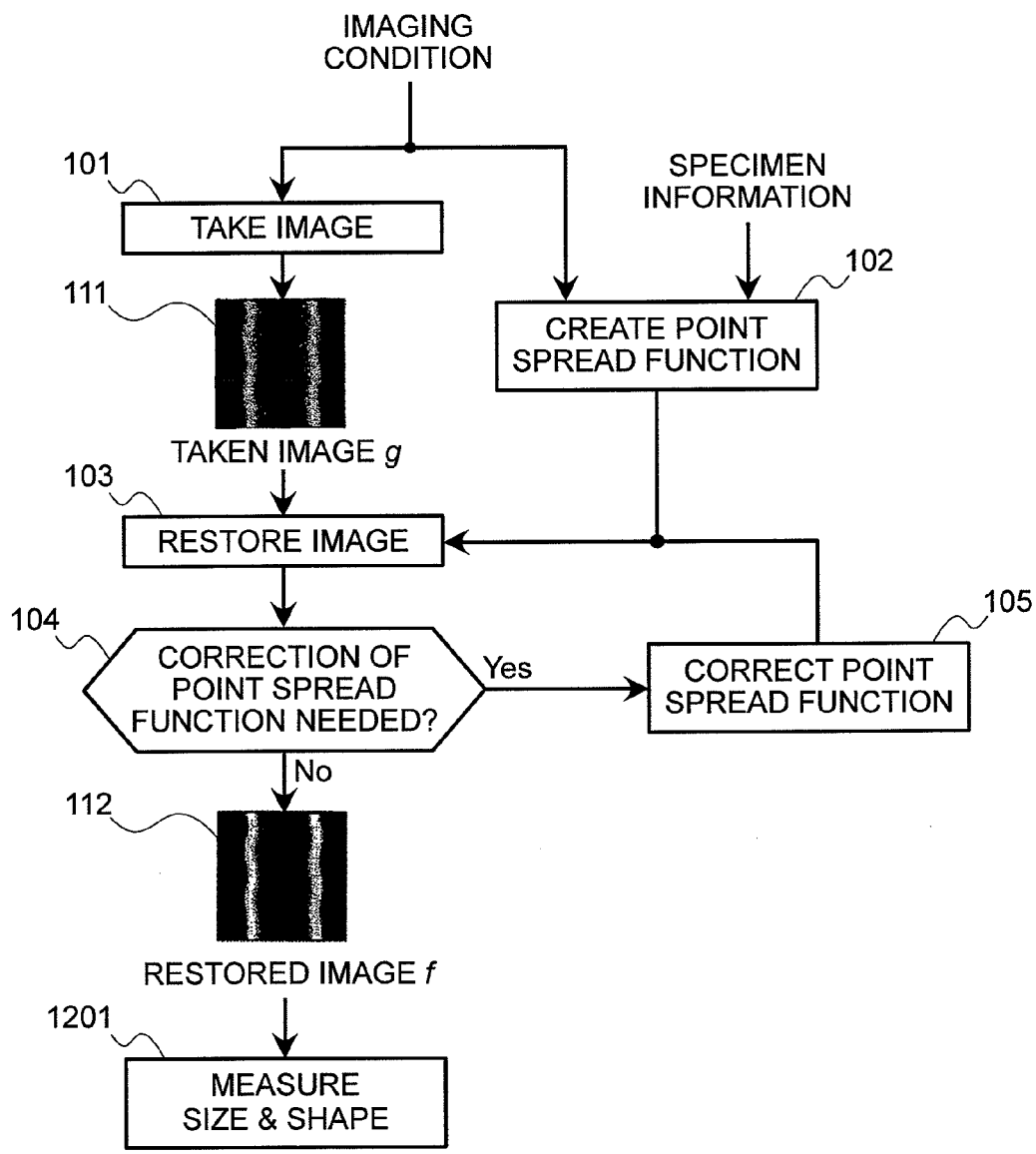
FIG. 16 shows one embodiment of a sequence of measuring the size and shape of a pattern by using the restored image in a semiconductor measuring SEM such as a measuring SEM.

FIG. 16 shows one embodiment of a sequence of measuring the pattern size and shape by using the restored image in the semiconductor measuring SEM such as the measuring SEM. The sequence of 101 to 105 is identical to that of FIG. 1. The restored image 112 is subjected at Step 1201 to the size measurement or shape measurement of the pattern contained in the image. This operation is performed in the measuring SEM or the like at the point (or the evaluation point), where the size measurement, the shape measurement or the like is to be performed. In the measuring SEM, the taken image is ordinarily produced by detecting the secondary electrons.

If the image is produced to have the higher luminosity coefficient for the larger number of secondary electrons, it is possible to obtain an image, which can form a linear region (or a white band) having a large luminosity coefficient in a pattern edge. The size measurement and the shape measurement of the pattern are performed by using the white band. However, there arises a problem that the image having the lower resolving power is caused to have the lower precision by the larger width of the white band. Therefore, the size measurement and the shape measurement of the pattern for the restored image can more improve the precision than the similar measurements on the taken image.

Examples of a sequence for automatically taking an evaluation point image in the semiconductor measuring SEM thereby to measure the size and the shape are shown in FIGS. 17A to 17D. The evaluation point image is frequently taken in a magnification as high as one hundred thousand or more, but is lower in the positional precision than the image region of the evaluation point image. At first, therefore, in the sequence of FIG. 17A, the image of the addressing point is taken at Step 1801 so as to adjust the positional precision, and the positional deviation is corrected at Step 1802 by using that taken image. Next, the image of the evaluation point is taken at Step 1803, and the taken image is subjected at Step 1804 to an image restoration thereby to produce the restored image. At Step 1805, that restored image is used to perform the size measurement and the shape measurement of the pattern contained in the image. The operations of Steps 1801 to 1805 are repeated for every target evaluation points. The restored image produced at Step 1804 can also be stored in a database 1820.

Figure 17A:
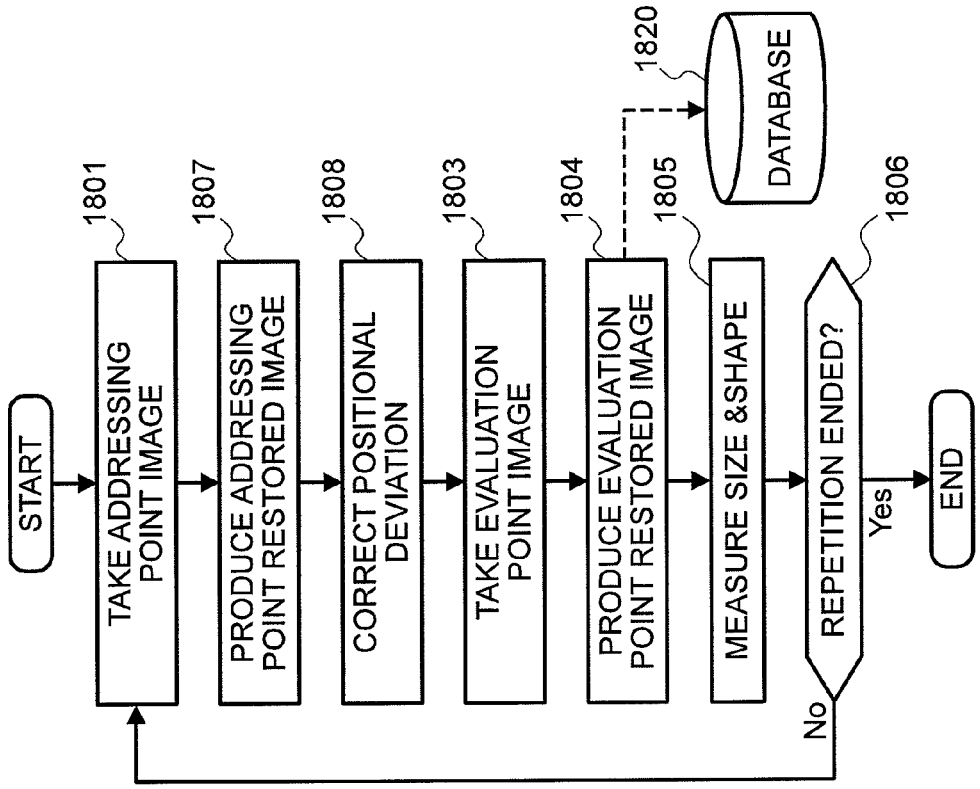
FIG. 17A is a sequence flow diagram for automatically taking an evaluation point image in the semiconductor measuring SEM thereby to measure the size and the shape.
Figure 17B:
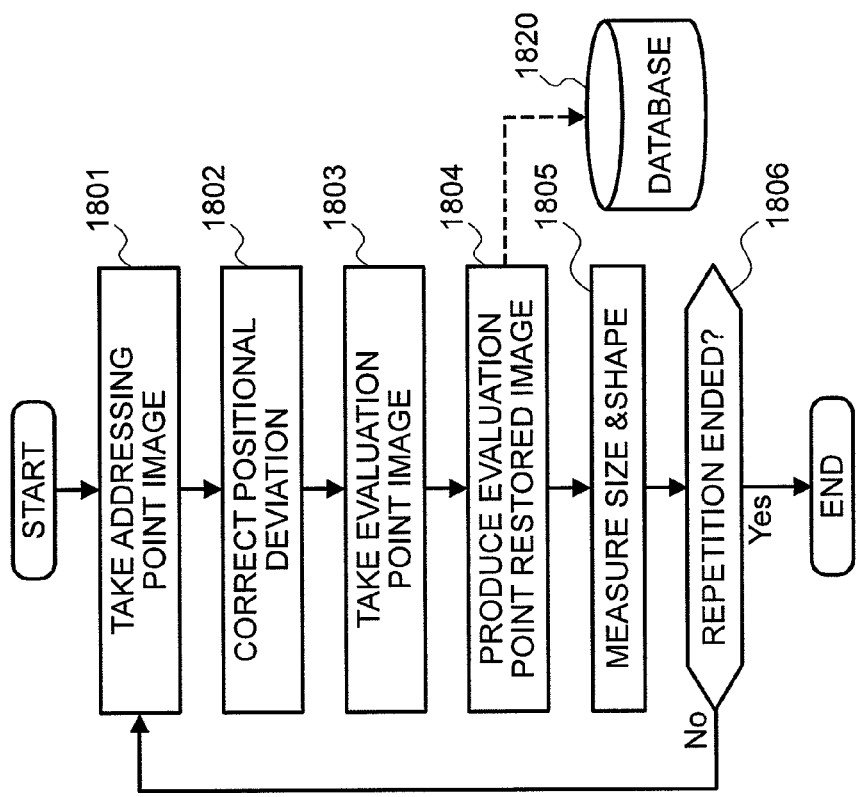
FIG. 17B is a measuring sequence flow diagram for restoring that image of an addressing point, which was taken at Step 1801, at Step 1807 to produce a restored image, and for correcting a positional deviation at Step 1808 by using that restored image.

In the sequence shown in FIG. 17A, on the other hand, the taken image obtained at Step 1801 of taking the addressing point image is used, as it is, to correct the positional deviation at Step 1802. In the sequence shown in FIG. 17B, on the other hand, the image of the addressing point taken at Step 1801 is restored at Step 1807 to produce the restored image, and this restored image is used at Step 1808 to correct the positional deviation. This sequence is especially effective for the case, in which the resolving power and the S/N ratio of the taken image of the addressing point are so low that the correction of the positional deviation is difficult.

Figure 17D:
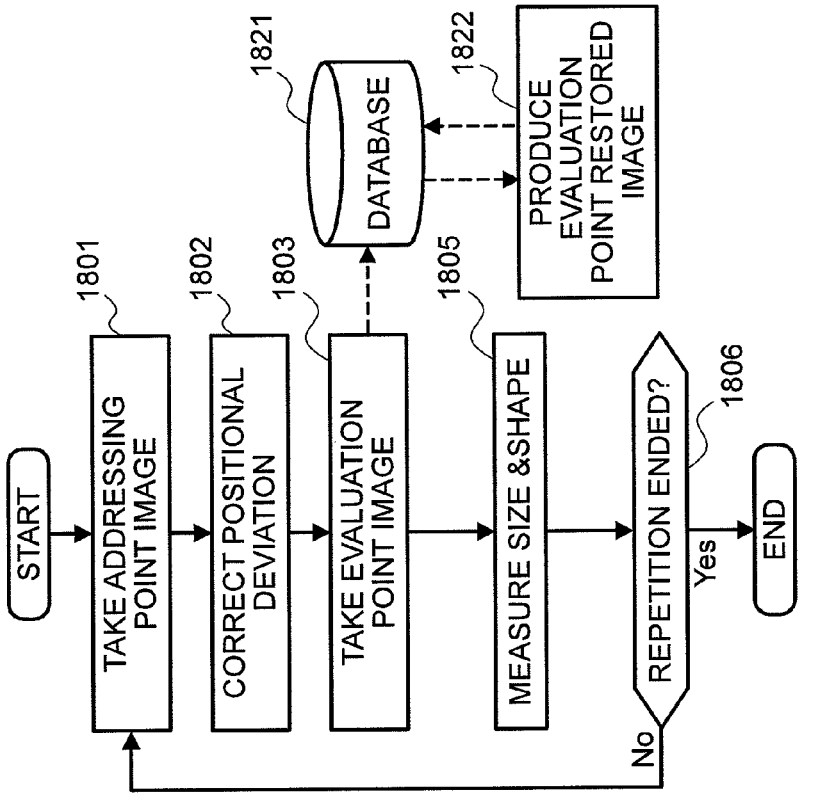
FIG. 17D is a measuring sequence flow diagram for producing the restored image, after the taken image of an evaluation point was stored in a database 1821, to the taken image separately read from that database at Step 1822.
Figure 17C:
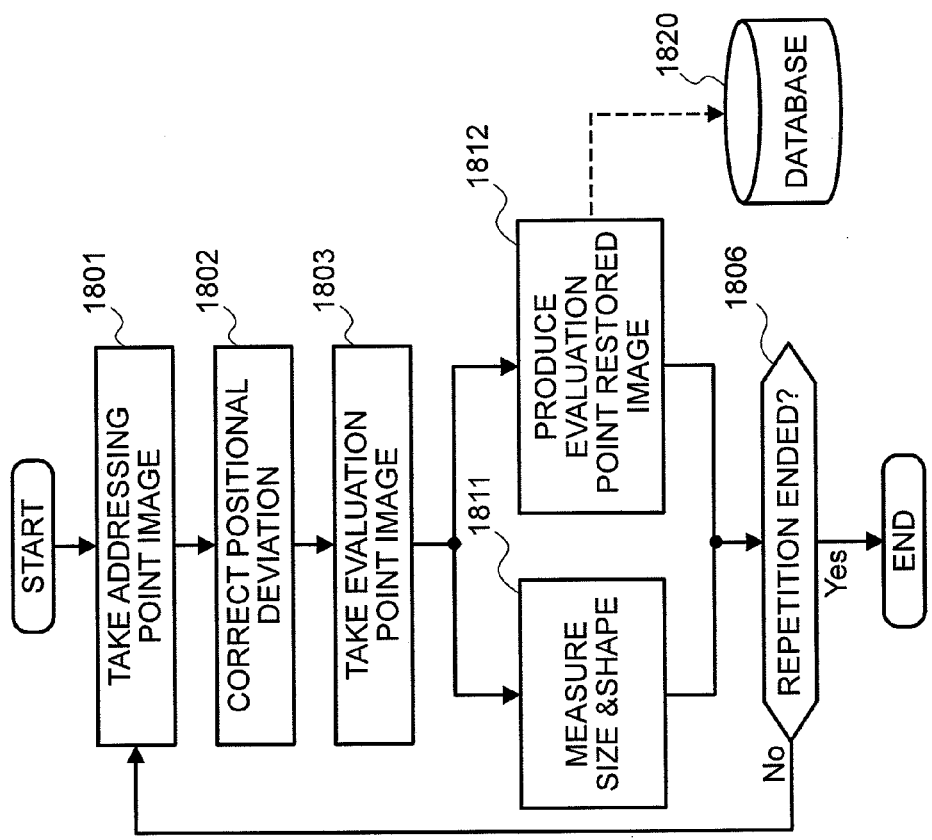
FIG. 17C is a measuring sequence flow diagram for performing the size measurement and the shape measurement of Step 1811 by using that taken image in place of that restored image.

In place of the sequence of FIG. 17A, on the other hand, the restored image is produced for the taken image of the evaluation point at Step 1812, as shown in FIG. 17C. However, the size measurement and the shape measurement of Step 1811 can be performed by using that taken image in place of that restored image. Moreover, after the taken image of the evaluation point is stored in a database 1821, as shown in FIG. 17D, the restored image can also be separately produced at Step 1822 for the taken image read from that database.

Figure 18:
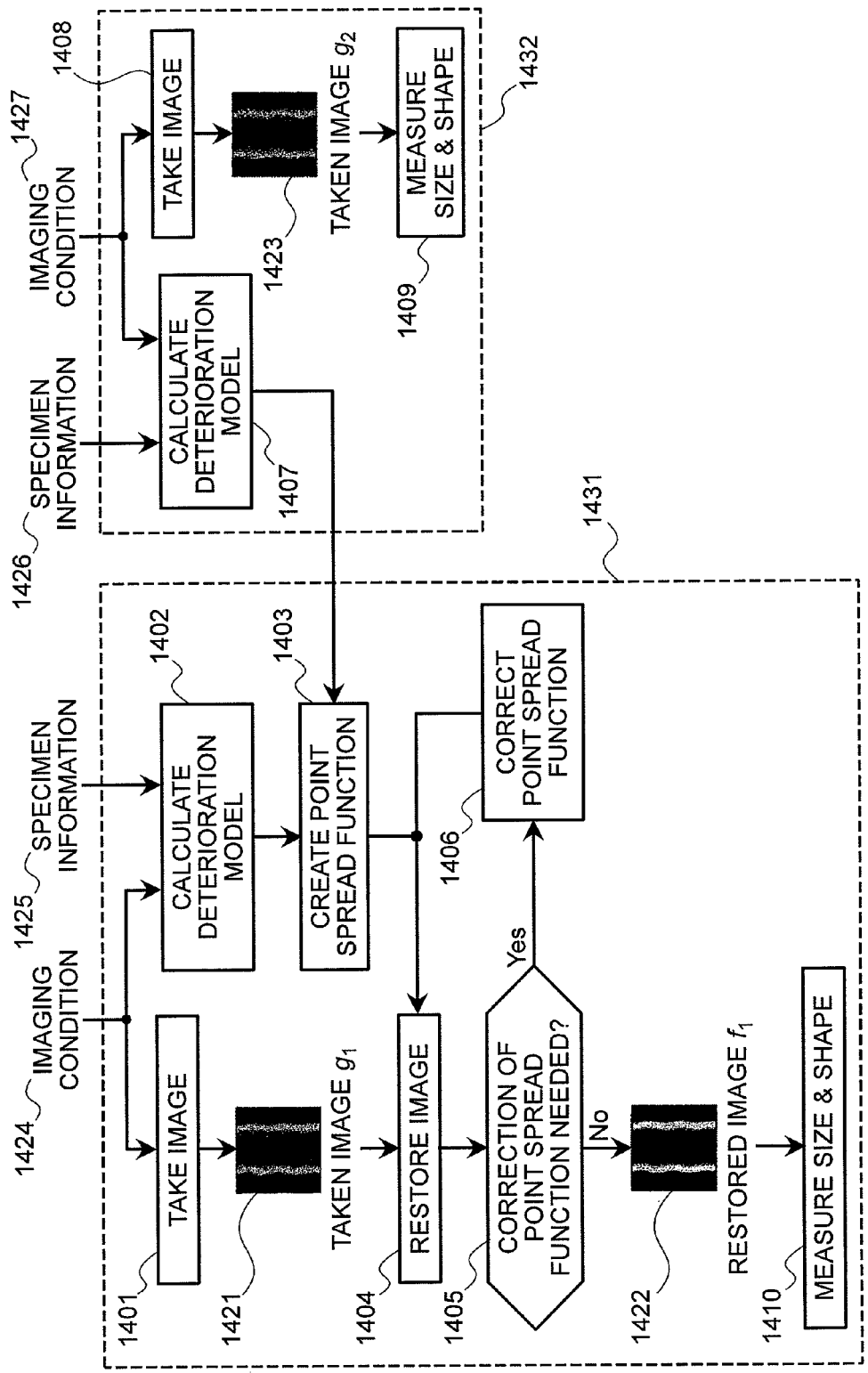
FIG. 18 shows one embodiment of a sequence of adjusting the resolving power by performing the restoration of a taken image of a low resolving power of two images taken under different imaging conditions, and then performing the pattern size and shape measurements.

FIG. 18 shows another embodiment of a sequence of performing the size and shape measurements of the pattern on the restored image. An image is taken under different imaging conditions 1424 and 1427 thereby to acquire individual taken images 1421 and 1423. The taken image 1421 is processed to adjust the resolving powers of the taken images 1421 and 1423. In the case where the resolving power of the taken image 1421 is higher than that of the taken image 1423, the resolving power of the taken image 1421 can be adjusted to that of the taken image 1423 by convoluting a low-pass filter in the taken image 1421. In the case where the resolving power of the taken image 1421 is lower, on the other hand, the taken image 1421 is subjected to an image restoration at Step 1404 so that its resolving power can be adjusted to that of the taken image 1423.

The taken images 1421 and 1423 may be taken either by a common device or by different devices. In a sequence 1432, an image is taken at first at Step 1408 on the basis of the preset imaging condition 1427 thereby to acquire a taken image $g_2$ at 1423. Next, the size measurement or the shape measurement of a pattern is performed at Step 1409. At Step 1407, on the other hand, that imaging condition and the specimen information are used at Step 1407 to calculate a deterioration model corresponding to a target resolving power deterioration factor. Likewise in a sequence 1431, an image is taken at Step 1401 on the basis of the imaging condition 1424 thereby to acquire a taken image $g_1$ at 1421. At Step 1402, moreover, the deterioration model is calculated from the imaging condition 1424 and the specimen information. After this, the point spread function A is created at Step 1403 from the deterioration model determined at Steps 1402 and 1407. In the case where the deterioration models determined at Steps 1402 and 1407 are $A_a$ and $A_b$, respectively, the point spread function A can be determined by using Formula (4).

Next, the restored image $f_1$ is determined at 1422 by performing the image restoration at Step 1404 by means of that point spread function A. If necessary, the point spread function can also be corrected at Steps 1405 and 1406. At Step 1406, the point spread function is corrected so that the resolving power of the restored image $f_1$ at 1422 may be identical to that of the taken image $g_2$ at 1423. After the correction of the point spread function was ended, the size measurement and the shape measurement of the pattern are performed at Step 1410 by using the restored image $f_1$.

In the embodiment of FIG. 18, the resolving power of the restored image $f_1$ is adjusted to that of the taken image $g_2$. However, the taken image $g_2$ may also be subjected to an image restoration so that the resolving power of the restored image $g_2$ and the resolving power of the restored image $g_1$ may be adjusted to each other. At Steps 1405 and 1406, the user may be inquired on whether or not the point spread function has to be corrected or on how to correct, or the correction may be automatically made on the basis of a reference designated in advance.

In an automatically correcting method, it is deemed necessary at Step 1405 to correct the point spread function if the square sum S, as expressed by the following Formula, of the differences between the restored image $f_1$ and the taken image $g_2$ is larger than a predetermined value. At the subsequent Step 1406, the width of the point spread function is corrected to become narrower, if the resolving power of the restored image $f_1$ is higher than that of the taken image $g_2$, and the width of the point spread function is corrected to become wider, if the resolving power of the restored image $f_1$ is lower:

$$S = \sum_{x,y} (f1(x, y) - g2(x, y))^2. \quad \text{(Formula 12)}$$

For the reference image to be compared with the restored image $f_1$ or the deterioration model outputted at Step 1407, moreover, it is unnecessary to use the actually obtained taken image or the deterioration model corresponding to the taken image, but a simulation model may be used for the reference image, for example. In place of the reference with the reference image, moreover, the resolving power or the like may be calculated from the restored image $f_1$, for example, and compared with the reference resolving power or the like.

According to this embodiment, the image of a pattern having a reduced noise component can be attained, and the pattern size measurement and the pattern shape measurement of higher precisions can be performed by using that image.

As the device state makes an aging change, the resolving power of the taken image may also change. Especially in the case where the stable resolving power has to be obtained for the applications of the size measurement and the shape measurement of the pattern, the state of the device has to be grasped at all times thereby to feed back the point spread function.

Figure 19:
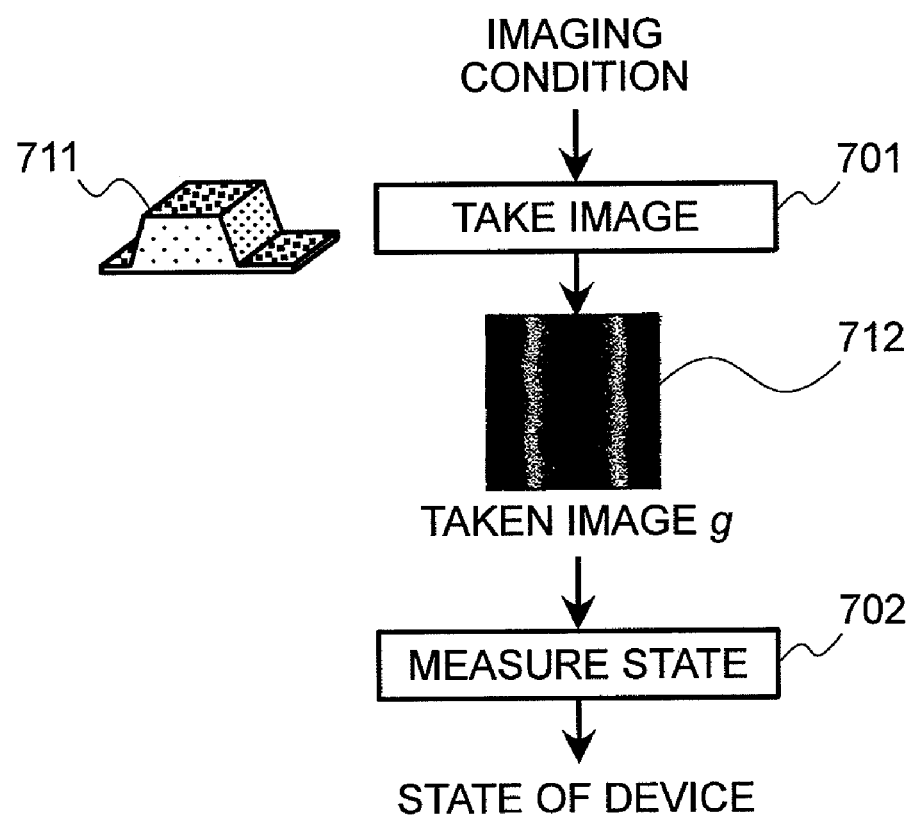
FIG. 19 shows one embodiment of a sequence of measuring the state of a device.

FIG. 19 shows one embodiment of a sequence of measuring the state of the device. First, samples such as 711 are prepared, and then the image of the samples is taken at the step 701 to obtain the taken image 712. Next, the state of the device is measured at the step 702. As the state of the device, for example, the resolving power of the taken image g and the size measurement of the pattern are measured. The state of the device is regarded as one of the taken image condition.

Figure 20:
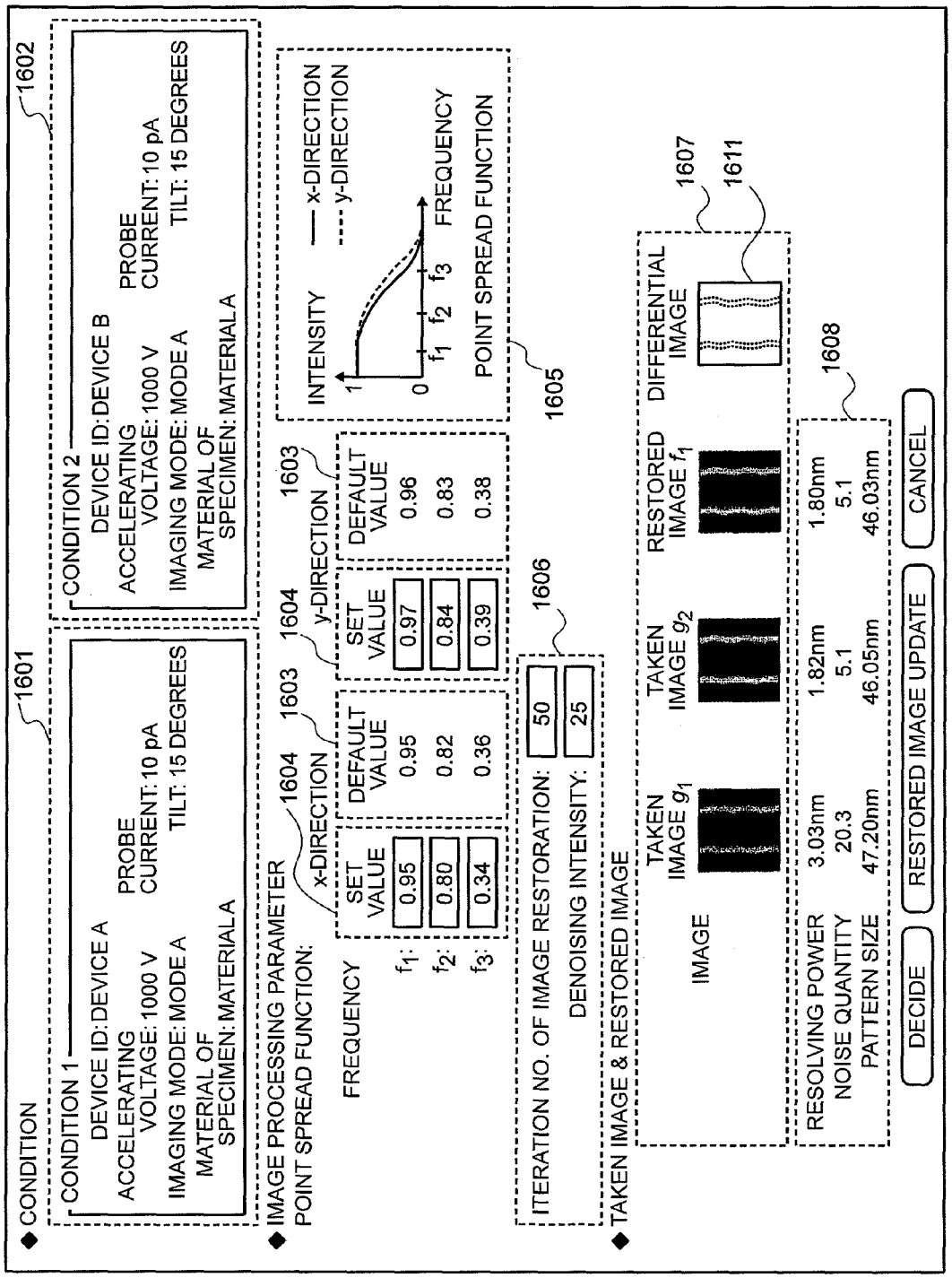
FIG. 20 shows one embodiment of a GUI screen for urging a user the method for correcting the point spread function.

In the point spread function correction or the Step 1406 of FIG. 18, a GUI screen for urging the user the correcting method of the point spread function A is shown in FIG. 20. There are a region 1601 for displaying the imaging condition 1424 and specimen information 1425 of FIG. 18, and a region 1602 for displaying the imaging condition 1427 and specimen information 1602. As in FIG. 18, moreover, there are a region 1605 for displaying the point spread function, a region 1603 for displaying the default values of parameters indicating that point spread function, and a region 1604 for setting parameters indicating that point spread function. Moreover, there may be a region 1606 for setting the processing parameters of the image restoration.

In the GUI screen of FIG. 20, moreover, there is a region such as a region 1607 for displaying the taken image $g_1$ at 1421, the taken image $g_2$ at 1423, and the restored image $f_1$ at 1422. In addition to these images, a differential image 1611 or the like between the taken image $g_2$ and the restored image $f_1$ may also be displayed to facilitate the matching of the taken image $g_2$ and the restored image $f_1$. There may also be a region 1608 for displaying the values such as the resolving power, the noise quantity and the pattern size, which can be calculated like the region 1108 from the individual images.

The foregoing embodiments 1 and 2 have been described on the case, in which the SEM is used as the scanning electron device. It is, however, apparent that a similar image processing method can also be applied to the case using the SIM.

Although the present invention has been specifically described on the basis of the best mode thereof, it should not be limited to the best mode for carrying out itself but can naturally be modified in various manners without departing from the gist thereof.

The invention may be embodied in other specific forms without departing from the spirit or essential characteristics thereof. The present embodiment is therefore to be considered in all respects as illustrative and not restrictive, the scope of the invention being indicated by the appended claims rather than by the following description and all changes which come within the meaning and range of equivalency of the claims are therefore intended to be embraced therein.

What is claimed is:

1. A scanning electron microscope device comprising:
    a charged particle beam irradiating system for irradiating and scanning a specimen having a pattern with a charged particle beam;
    a charged particle detecting system for detecting charged particles of the kind identical to or different from charged particles emitted from said specimen, which was irradiated and scanned with the charged particle beam by said charged particle beam irradiating system;
    image acquiring means for acquiring a charged particle image of said specimen by processing a signal detected by said charged particle detecting system;
    image processing means for processing the charged particle image of said specimen acquired by said image acquiring means; and
    storage means for storing plural parameters corresponding to plural imaging conditions for calculating point spread functions,
    wherein said image processing means determines a restored image of the acquired image by using a point spread function, which is calculated based on a parameter being selected from the stored plural parameters corresponding to plural imaging conditions as the one corresponding to an imaging condition of at least one of an acceleration voltage and a probe current for the acquired image, and
    wherein said point spread function is a function expressing a resolving power deterioration model determined from a dispersion distribution of the charged particles in the specimen.

2. A scanning electron microscope device according to claim 1,
    wherein said image processing means performs, by using the restored image determined, any of a defect detection of a pattern on said specimen, a defect classification of the pattern on said specimen, and a measurement of the size and shape of the pattern on said specimen.

3. A scanning electron microscope device according to claim 1,
    wherein said image processing means determines the restored image from said acquired image by using said point spread function and information of a noise component of said acquired image, with the noise component independent from said point spread function.

4. A scanning electron microscope device according to claim 1,
wherein said point spread function is created by using two or more kinds of different types of imaging conditions, each imaging condition including at least an acceleration voltage and a probe current, and
wherein said point spread function is determined from a difference between a first resolving power deterioration model which expresses a distribution in the specimen calculated by using a first imaging condition and a second resolving power determination model which expresses a dispersion distribution in the specimen calculated by using a second imaging condition.

5. A scanning electron microscope device according to claim 1, wherein the stored plural parameters are plural beam intensity distributions.

6. A scanning electron microscope device according to claim 1, wherein the stored plural parameters are parameters being changeable according to imaging conditions for calculating a beam intensity distribution.

7. A scanning electron microscope device according to claim 1, wherein dispersion of the charged particles in the specimen is calculated using at least a shape information and a material information of the specimen.

8. A method for processing an image acquired by a scanning electron microscope device, the method comprising:
irradiating and scanning a specimen having a pattern with a charged particle beam focused by using the scanning electron microscope device, to detect charged particles produced from said specimen thereby to acquire a charged particle image of said specimen;
processing the charged particle image of said acquired specimen; and
storing plural parameters corresponding to plural imaging conditions for calculating point spread functions,
wherein a point spread function, which is calculated based on a parameter selected from the stored plural parameters is selected as corresponding to an imaging condition of at least one of an acceleration voltage and a probe current for the acquired image is used to determine a restored image of the acquired charged particle image, and
wherein said point spread function is a function expressing a resolving power deterioration model determined from a dispersion distribution of the charged particles in the specimen.

9. A method according to claim 8,
wherein said image processing means performs, by using the restored image determined, any of a defect detection of a pattern on said specimen, a defect classification of the pattern on said specimen, and a measurement of the size and shape of the pattern on said specimen.

10. A method according to claim 8,
wherein said image processing means determines the restored image from said acquired image by using said point spread function and information of a noise component of said acquired image, with the noise component independent from said point spread function.

11. A method according to claim 8,
wherein said point spread function is created by using two or more kinds of imaging conditions, each imaging condition including at least an acceleration voltage and a probe current, and
wherein said point spread function is determined from a difference between a first resolving power deterioration model which expresses a distribution in the specimen calculated by using a first imaging condition and a second resolving power determination model which expresses a dispersion distribution in the specimen calculated by using a second imaging condition.

* * * * *